US009370585B2

(12) United States Patent
Sancilio et al.

(10) Patent No.: US 9,370,585 B2
(45) Date of Patent: *Jun. 21, 2016

(54) STABLE MICELLES OF MIXED FATTY ACIDS

(71) Applicant: Sancilio & Company, Inc., Riviera Beach, FL (US)

(72) Inventors: Frederick Sancilio, Palm Beach Gardens, FL (US); Peter Persicaner, Boca Raton, FL (US); Janice Cacace, St. Petersburg, FL (US); Mohand Dahim, Gaithersburg, MD (US)

(73) Assignee: Sancilio & Company, Inc., Riviera Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/808,777

(22) Filed: Jul. 24, 2015

(65) Prior Publication Data

US 2015/0328153 A1 Nov. 19, 2015

Related U.S. Application Data

(63) Continuation of application No. 14/456,750, filed on Aug. 11, 2014, which is a continuation of application No. PCT/US2013/030211, filed on Mar. 11, 2013.

(60) Provisional application No. 61/618,161, filed on Mar. 30, 2012.

(51) Int. Cl.
*A61K 9/00* (2006.01)
*A61K 31/232* (2006.01)
*A61K 47/26* (2006.01)
*A61K 47/10* (2006.01)
*A61K 47/48* (2006.01)
*A61K 47/34* (2006.01)
*A61K 47/06* (2006.01)
*A61K 31/355* (2006.01)
*A61K 45/06* (2006.01)
*A61K 47/44* (2006.01)
*A61K 47/22* (2006.01)
*A61K 9/107* (2006.01)
*A61K 9/48* (2006.01)
*A61K 31/05* (2006.01)
*A61K 31/7024* (2006.01)

(52) U.S. Cl.
CPC ............ *A61K 47/488* (2013.01); *A61K 9/1075* (2013.01); *A61K 9/4858* (2013.01); *A61K 31/05* (2013.01); *A61K 31/232* (2013.01); *A61K 31/355* (2013.01); *A61K 31/7024* (2013.01); *A61K 45/06* (2013.01); *A61K 47/06* (2013.01); *A61K 47/10* (2013.01); *A61K 47/22* (2013.01); *A61K 47/26* (2013.01); *A61K 47/34* (2013.01); *A61K 47/44* (2013.01); *A61K 47/48215* (2013.01)

(58) Field of Classification Search
None
See application file for complete search history.

(56) References Cited

U.S. PATENT DOCUMENTS

| | | |
|---|---|---|
| 4,513,008 A | 4/1985 | Revici et al. |
| 4,992,476 A | 2/1991 | Geria |
| 5,502,077 A | 3/1996 | Breivik et al. |
| 6,121,210 A | 9/2000 | Taylor |
| 6,284,268 B1 | 9/2001 | Mishra et al. |
| 7,041,324 B2 | 5/2006 | Myhre |
| 7,642,287 B2 | 1/2010 | Guzman et al. |
| 7,919,526 B2 | 4/2011 | Rozen et al. |
| 8,071,646 B2 | 12/2011 | Feuerstein et al. |
| 8,324,276 B2 | 12/2012 | Bryhn |
| 8,377,494 B2 | 2/2013 | Behnam |
| 8,529,979 B2 | 9/2013 | Abril et al. |
| 8,563,608 B2 | 10/2013 | Manku et al. |
| 8,609,726 B2 | 12/2013 | Bryhn |
| 8,618,166 B2 | 12/2013 | Osterloh et al. |

(Continued)

FOREIGN PATENT DOCUMENTS

| | | |
|---|---|---|
| CN | 101380358 A | 3/2009 |
| EP | 1782807 A1 | 5/2007 |

(Continued)

OTHER PUBLICATIONS

Kris-Etherton, et al. Omega-3 Fatty Acids and Cardiovascular Disease: New Recommendations From the American Heart Association. Arterioscler Thromb Vase Biol. 2003;23: 151-152 doi: 10.1161/01.ATV.0000057393.97337.AE.

Holub, Bruce J. Docosahexaenoic acid (DHA) and cardiovascular disease risk factors. Prostaglandins, Leukotrienes and Essential Fatty Acids 81 (2009) 199-204.

Raatz, S. K. Enhanced Absorption of n-3 Fatty Acids from Emulsified Compared with Encapsulated Fish Oil. J Am Diet Assoc. 2009; 109:1076-1081. doi: 10.1016/j.jada2009.03.06.

(Continued)

*Primary Examiner* — Jessica Worsham
(74) *Attorney, Agent, or Firm* — Nexsen Pruet, PLLC; Robert P. Mino; Ferris H. Lander

(57) ABSTRACT

Compositions including at least one Omega-3 fatty acid ester and at least one surface active agent are provided; wherein the compositions form micelles when in contact with an aqueous medium. Also provided is a method of administering to a subject such a composition, wherein the at least one Omega-3 fatty acid ester forms micelles when in contact with an aqueous medium, and the bioavailability of the at least one Omega-3 fatty acid ester is substantially independent of a food effect. The compositions are useful for treating cardiovascular conditions or disorders in a subject and for reducing side effects associated with the ingestion of Omega-3 fatty acid esters. Further provided are also various dosage forms for administering the compositions and use of the compositions in functional foods. Provided herein are also kits with instructions on how to administer the compositions.

24 Claims, 4 Drawing Sheets

(56) References Cited

U.S. PATENT DOCUMENTS

| | | | |
|---|---|---|---|
| 8,618,168 | B2 | 12/2013 | Fuji et al. |
| 8,691,871 | B2 | 4/2014 | Osterloh et al. |
| 9,056,088 | B2 | 6/2015 | Osterloh et al. |
| 2005/0074414 | A1 | 4/2005 | Tamarkin et al. |
| 2005/0075407 | A1 | 4/2005 | Tamarkin et al. |
| 2005/0118254 | A1 | 6/2005 | Choi et al. |
| 2005/0171200 | A1 | 8/2005 | Calder et al. |
| 2006/0009522 | A1 | 1/2006 | Dana et al. |
| 2006/0165735 | A1 | 7/2006 | Abril et al. |
| 2006/0210622 | A1 | 9/2006 | Pace et al. |
| 2006/0211763 | A1 | 9/2006 | Fawzy et al. |
| 2006/0223737 | A1 | 10/2006 | Sebillotte-Arnaud et al. |
| 2007/0104779 | A1 | 5/2007 | Rongen et al. |
| 2007/0112071 | A1 | 5/2007 | Bryhn et al. |
| 2007/0259957 | A1 | 11/2007 | Ueshima et al. |
| 2008/0058418 | A1 | 3/2008 | D'Angelo et al. |
| 2008/0102131 | A1 | 5/2008 | Nagira et al. |
| 2008/0138293 | A1 | 6/2008 | Tamarkin et al. |
| 2008/0255247 | A1 | 10/2008 | Sagalowicz et al. |
| 2008/0275119 | A1 | 11/2008 | Puder et al. |
| 2008/0306154 | A1 | 12/2008 | Svensson et al. |
| 2009/0011012 | A1 | 1/2009 | Baum |
| 2009/0053306 | A1 | 2/2009 | Agarwal et al. |
| 2009/0149533 | A1 | 6/2009 | Almarsson et al. |
| 2009/0182049 | A1 | 7/2009 | Opheim |
| 2010/0062057 | A1 | 3/2010 | Berge et al. |
| 2010/0305045 | A1 | 12/2010 | Yu |
| 2011/0045050 | A1 | 2/2011 | Elbayoumi et al. |
| 2011/0118351 | A1 | 5/2011 | Berl |
| 2011/0262534 | A1 | 10/2011 | Berge et al. |
| 2012/0053242 | A1 | 3/2012 | Cela Lopez |
| 2012/0093922 | A1 | 4/2012 | Manku et al. |
| 2012/0207800 | A1 | 8/2012 | Abu-Saker et al. |
| 2012/0225945 | A1 | 9/2012 | Hustvedt et al. |
| 2013/0203701 | A1 | 8/2013 | Leighton |
| 2014/0004186 | A1 | 1/2014 | Hustvedt et al. |
| 2014/0050807 | A1 | 2/2014 | Leighton |
| 2014/0154310 | A1 | 6/2014 | Osterloh et al. |
| 2014/0155455 | A1 | 6/2014 | Osterloh et al. |
| 2014/0186503 | A1 | 7/2014 | Mattson et al. |

FOREIGN PATENT DOCUMENTS

| | | |
|---|---|---|
| EP | 1946755 A1 | 7/2008 |
| EP | 2433630 A1 | 3/2012 |
| WO | 9929316 A1 | 6/1999 |
| WO | 0048592 A1 | 8/2000 |
| WO | 2011048493 A1 | 4/2011 |
| WO | 2012032414 A2 | 3/2012 |
| WO | 2012032415 A2 | 3/2012 |
| WO | 2012032417 A2 | 3/2012 |
| WO | 2013123466 A1 | 8/2013 |

OTHER PUBLICATIONS

Kris-Etherton, et al. Fish Consumption, Fish Oil, Omega-3 Fatty Acids, and Cardiovascular Disease. Circulation. 2002;106:2747-2757. doi: 10.1161/01.CIR.0000038493.65177.94.
Weitz, D. et al. Fish Oil for the Treatment of Cardiovascular Disease. Cardiol Rev. 2010; 18(5): 258-263. doi:10.1097/CRD.Ob013e3181ea0de0.
Breslow, J.L. n-3 Fatty acids and cardiovascular disease. Am J Clin Nutr 2006;83(suppi):1477S-82S.
Fatouros D.G. et al. Clinical studies with oral lipid based formulations of poorly soluble compounds Therapeutics and Clinical Risk Management 2007:3(4) 591-604.
Fomuso, L.D. et al. Effect of Emulsifier on Oxidation Properties of Fish Oil-Based Structured Lipid Emulsions. J. Agric. Food Chem. 2002,50, 2957-2961.
Garaiova, I. et al. A randomised cross-over trial in healthy adults indicating improved absorption of omega-3 fatty acids by pre-emulsification. Nutrition Journal 2007, 6:4 doi:10.1186/1475-2891-6-4.
Bauer, I. et al. Omega-3 Fatty Acids Modify Human Cortical Visual Processing—A Double-Blind, Crossover Study. Omega-3 Fatty Acids Modify Human Cortical Visual Processing—A Double-Blind, Crossover Study. PLoS ONE. 2011. 6 (12): e28214. doi:10.1371/journal.pone.0028214.
Stone, N.J. Fish Consumption, Fish Oil, Lipids, and Coronary Heart Disease. Retrieved from http://circ.ahajournals.org/conten/94/9/2337.full?ijkey=461 a04097321 c4af646235a3c4ca9a2dec26ecdc &keytype2=tf_ipsecsha on Sep. 17, 2014. Article originally published Jul. 1996.
Lee, K. Beware the 'other' Vitamin Supplement Ingredients. Retrieved from http://www.articlesbase.com/supplements-and-vitamins-articles/beware-the-other-vitamin-supplement-ingredients-551837.html on Sep. 17, 2014. Article originally published Sep. 8, 2007.
The Best Omega-3 brochure retrieved from http://thebestomega3.com/ on Sep. 17, 2014.
Vin Kutty, MS. Lovaza vs Fish Oil Supplements: A Side-by-Side Comparison. Retrieved from http://www.omegavia.com/lovaza-vs-fish-oil/ on Sep. 17, 2014. Article originally published Jun. 5, 2010.
"Microencapsulating fish oil" retrieved from http://www.biotechlearn.org.nz/focus_stories/fish_oil_in_functional_food/microencapsulating_fish_oil on Sep. 17, 2014. Article originally published Jul. 17, 2009.
Product details for "PlusKenko" retrieved from http://www.miragedistribution.com/pluskenko.html on Sep. 17, 2014.
Product details for "ProOmega-D Xtra" retrieved from http://www.nordicnaturals.com/en/Products/Product_Details/515/?ProdiD= 1618 on Sep. 17, 2014.
"The EPA/DHA Ratio in Fish Oil" retrieved from http://www.livestrong.com/article/495090-the-epa-dha-ratio-in-fish-oil/ on Sep. 17, 2014.
Product details for "WIN0meg3Complex" retrieved from http://winomega3.com/ on Sep. 17, 2014.
Product brochure for NovaSOL Omega retrieved from http://www.aquanova.de/media/public/pdf_produkte%20unkosher/NovaSOL_Omega_AAG_fin.pdf on Sep. 18, 2014.
Product Data Sheet for NovaSol Omega retrieved from http://www.aquanova.de/media/public/pds/PDS_EW0093_22_NovaSOL%20Omega.pdf on Sep. 18, 2014.
Product brochure for "Omega3-6-9 Emulsion" retrieved from http://web.archive.org/web/20131013023047/http:i/www.bio- genesis.com/productpages/omega-369-emulsion/omega-369-emulsion.html on Sep. 18, 2014.
Product brochure for NanoEPA DHA retrieved from http ://web.archive .org/web/20121 027093701 /http:/ /www.biopharmasci.com/content.cfm?n=products&id=8 on Sep. 18, 2014.
Product information for "Minami Nutrition Supercritical Omega 3 Fish Oils" retrieved from http://www.transformyourhealth.com/gardenoflife/minamiintroduction.html on Sep. 18, 2014.
Ayanda As. Bioavailability Study of Long Chain Omega-3 Fatty Acids From a Gastric Stable Emulsion. Retrieved from http://clinicaltrials.gov/show/NCT01061554 on Sep. 18, 2014.
Product Information for Sancilio & Company, Inc.'s Ocean Blue Pharmaceutical Grade Omega Power, Omega• 3 Minicaps, Omega• 3 +D3 Minicaps, and DHA Minicaps, May 30, 2013.
Product Information for Sancilio & Company, Inc.'s Ocean Blue Professional Omega• 3 2100, Jul. 10, 2013.
Martin, CR et al., The safety and efficacy of oral docosahexaenoic acid supplementation for the treatment of primary sclerosing cholangitis—a pilot study; Aliment Pharmacol Ther. Author manuscript; PMC; Jan. 2012 Jul. 18; pp. 1-17.
SanGiovanni et al., ω-3 Long-chain polyunsaturated fatty acid intake and 12-y incidence of neovascular age-related macular degeneration and central geographic atrophy: AREDS report 30, a prospective cohort study from the Age-Related Eye Disease Study; The American Journal of Clinical Nutrition; Dec. 2009; pp. 1601-1607.
Lewis, Michael et al., Therapeutic use of omega-3 fatty acids in severe head trauma; Am J Emerg Med; Author manuscript; PMC, Jan. 2013; pp. 1-6.
Bougnoux, P. et al., Improving outcome of chemotherapy of metastic breast cancer by docosahexaenoic acid: a phase II trial; British Journal of Cancer (Nov. 2009), pp. 1978-1985.

(56) References Cited

OTHER PUBLICATIONS

Mills, James D. et al., Dietary Supplementation With the Omega-3 Fatty Acid Docosahexaenoic Acid in Traumatic Brain Injury; Neurosurgery, Issue: vol. 68(2), Feb. 2011, pp. 474-481.

Nobili, V. et al., Docsahexaenoic acid for the treatment of fatty liver: Randomised controlled trial in children; Nutrition, Metabolism & Cardiovascular Diseases (Dec. 2012) vol. 23, pp. 1066-1070.

Kelley, D.S. et al., DHA Supplementation Decreases Serum C-Reactive Protein and Other Markers of Imflammation in Hypertriglyceridemic Men; The Journal of Nutrition Nutrition and Disease; Jan. 2009; pp. 495-501.

Depner, C. M. et al.; Menhaden Oil Decreases High-Fat Diet-Induced Markers of Hepatic Damage, Steatosis, Inflammation, and Fibrosis in Obese Ldlr Mice; The Journal of Nutrition Nutrition and Disease; Jun. 2012; pp. 1495-1503.

Parker, Helen M. et al.; Omega-3 supplementation and non-alcoholic fatty liver disease: A systematic review and meta-analysis; Journal of Hepatology (2012) vol. 56; pp. 944-951.

Logan, Alan C.; Omega-3 fatty acids and major depression: A primer for the mental health professional; BioMed Central; Nov. 9, 2004; pp. 1-8.

Morishita, Mariko et al.; Pluronic® F-127 gels incorporating highly purified unsaturated fatty acids for buccal delivery of insulin; International Journal of Pharmaceutics 212 (2001); pp. 289-293.

Product Information for Neptune Krill Oil's Unique Properties; Retrieved from http://www.nowfoods.com/Products/FAQs/081008.htm on Jul. 20, 2015.

Zanarini, Mary C. et al., Omega-3 Fatty Acid Treatment of Women With Borderline Personality Disorder: A Double-Blind, Placebo-Controlled Pilot Study; The American Journal of Psychiatry; Jan. 2003; 160,1: ProQuest Social Social Sciences Premium Collection; pp. 167-169.

Sallis, Hannah et al.; Perinatal depression and omega-3 fatty acids: A Mendelian randomisation study; Journal of Affective Disorders 166 (2014; pp. 124-131).

Richardson, Alexandra J. et al.; Docosahexaenoic Acid for Reading, Cognition and Behavior in Children Aged 7-9 Years: A Randomized, Controlled Trial (The DOLAB Study); PLOS ONE; Sep. 2012; vol. 7; Issue 9; pp. 1-14.

Lewis, Michael D. et al.; Suicide Deaths of Active Duty U.S. Military and Omega-3 Fatty Acid Status: A Case Control Comparison; J Clin Psychiatry; Author manuscript; PMC Jan. 17, 2012; pp. 1-14.

Chew, Emily Y. et al.; The Age-related Eye Disease Study 2 (AREDS2); The American Academy of Ophthalmology (2012); pp. 2282-2289.

STABLE MICELLES OF MIXED FATTY ACIDS

CROSS REFERENCE TO RELATED APPLICATIONS

This patent application is a continuation of U.S. patent application Ser. No. 14/456,750, filed Aug. 11, 2014, which is a continuation of and claims priority to PCT International Patent Application No. PCT/US13/30211 entitled Omega-3 Fatty Acid Ester Compositions filed on Mar. 11, 2013 and which is related and claims priority to U.S. Provisional Patent Application No. 61/618,161 filed Mar. 30, 2012; the entire disclosures of which are specifically incorporated by reference herein in their entirety.

BACKGROUND

According to the World Health Organization's (WHO) fact sheet on Cardiovascular Diseases (CVDs), CVDs are the number one cause of death globally. (Fact Sheet No. 317, September 2012 accessed at www.who.int/mediacentre/factsheets/fs317/en/index.html on Jan. 31, 2013. The WHO estimates that an estimated 17.3 million people died from CVDs in 2008, representing 30% of all global deaths. Of these deaths, an estimated 7.3 million were due to coronary heart disease (CHD) and 6.2 million were due to stroke. The WHO also estimates that by 2030, almost 25 million people will die from CVDs, mainly from heart disease and stroke. The Global Burden of Disease Study estimates that the developing countries contributed 3.5 million of the 6.2 million global deaths from CHD in 1990. (Murray C J L and Lopez A D. The Global Burden of Disease A Comprehensive Assessment of Mortality and Disability from Disease, Injuries and Risk Factors in 1990 and Projected to 2020. Boston, Ma Harvard University Press; 1996). The projections estimate that these countries will account for 7.8 million of the 11.1 million deaths due to CHD in 2020. The developed countries are not immune to CHD. For example, in the USA and Europe, CHD remains the largest single cause of death and disability. In 2005, CHD caused approximately 1 of every 5 deaths in the USA. (Heron M P, et. al. Deaths preliminary data for 2006. Natl. Vital. Stat. Rep. 2008; 56:1-52.) According to the Centers for Disease Control and Prevention it is the leading cause of death in America. Approximately 37% of people who develop a coronary event in a given year will die from it. While major reductions in CVD related mortality have been achieved in Europe, CVD still accounts for 54% of all deaths in women and 43% of all deaths in men.

CVD is associated with many risk factors. Of these risk factors, hyperlipidemia (e.g., hypertriglyceridemia) and hypercholesterolemia are significant indicators of CVD. As such, dietary supplements, nutraceuticals, and prescribed drugs containing Omega-3 fatty acid esters, such as the ethyl esters of EPA and DHA, are currently used for the treatment of CVD and, in particular, for the reduction of elevated triglycerides.

However, administration of dietary supplements, nutraceuticals, and prescribed drugs containing Omega-3 fatty acid esters presents significant challenges. For example, current dietary supplements, nutraceuticals, and prescribed drugs containing Omega-3 fatty acid esters have variable absorption and efficacy when orally administered. In particular, current compositions have a pronounced "food effect," with poor absorption when taken while fasting or with a low fat meal. When taken with fatty foods, the absorption of Omega-3 fatty acid esters improves, due in part to the presence of bile salts that are released in the intestines, which aid absorption of Omega-3 fatty acid esters.

To overcome low absorption, patients can be dosed with compositions having greater amounts of Omega-3 fatty acid esters, but there are practical limitations to this approach due to the side effects that are commonly associated with such compositions. The oxidative degradation of Omega-3 fatty acid esters that occurs over time can result in an unpleasant aftertaste following administration, especially when consumed in large quantities. Burping and stomach upset are further unpleasant side effects associated with the consumption of Omega-3 fatty acid esters. Following consumption, Omega-3 fatty acid esters tend to float on top of liquid contents in the stomach, forming a layer that prevents the passage of small gas bubbles. When sufficient gas has built up to overcome the surface tension of the oil layer, a person burps. The burps usually contain a fishy taste and smell.

Accordingly, side effects associated with the administration of current compositions comprising Omega-3 fatty acid esters (e.g., susceptibility to the food effect, large doses to attain efficacy, and the resulting aftertaste, unpleasant smell, and burping) are known to significantly reduce patient compliance.

While practicing a healthy lifestyle may reduce the incidence of CVD, new therapeutic approaches to manage CVD are warranted. These new approaches might include the discovery of new drugs or improve upon current medications used to treat CVD. The discovery of new drugs, however, comes at a high price with no certainty of eventual success. Accordingly, new or more efficient ways of delivering current medications with a proven safety and efficacy profile should be developed. Thus, there is a need for improved compositions comprising Omega-3 fatty acid esters, such as the ethyl esters of EPA and DHA, that are less susceptible to food effect and which attain high efficacy at lower doses. Ideally, such improved compositions would minimize or eliminate an unpleasant smell and/or an unpleasant aftertaste, and/or burping in the patient. Such an improved composition with reduced side effects would improve patient compliance and more effectively treat the risk factors related to cardiovascular disease.

SUMMARY

In all of the embodiments provided herein, all of the compositions are free of Omega-3 free fatty acids. Provided herein, in certain embodiments, are compositions comprising EPA and DHA esters in combination with at least one surface active agent. In certain embodiments, the ratio of EPA ester to DHA ester is from more than 2:1 to not more than 3.4:1. Certain embodiments provide for the ratio of the EPA ester to the DHA ester to be from about 2:1 to about 3.4:1. Provided herein, in certain embodiments, are compositions comprising at least one Omega-3 fatty acid ester and at least one surface active agent. In certain embodiments, the Omega-3 fatty acid ester is selected from the group consisting of hexadecatrienoic acid, α-linolenic acid, stearidonic acid, eicosatrienoic acid, eicosapentaenoic acid, heneicosapentaenoic acid, docosapentenoic acid, docosahexaenoic acid, tetracosapentenoic acid, tetracosahexaenoic acid, or combinations thereof. Certain embodiments provide for compositions comprising the ethyl ester derivative of said Omega-3 fatty acid ester, optionally in combination with at least one surface active agent, at least one terpene, at least one antioxidant, or combinations thereof. Certain embodiments also provide for combinations of different Omega-3 fatty acid esters in ratios of from about 2:1 to about 3.4:1. Other embodiments call for the ratio to be more than 2:1 to not more than 3.4:1. Typically, the ratio is about 2.4:1. Certain embodiments provide a method for treating a variety of conditions or disorders that can be treated by administering said Omega-3 fatty acid esters in compositions described herein comprising the described ratios, optionally with at least one surface active agent, at least one terpene, at least one antioxidant, or combinations thereof. The compositions described herein minimize several side effects found in currently marketed compositions containing Omega-3 fatty acid esters that can deter a human subject from complying with dosing regimen necessary to treat a condition or disorder treatable by administration of Omega-3 fatty acid esters. In certain embodiments, the bioavailability of said Omega-3 fatty acid esters when administered as certain compositions described herein is substantially the same when administered with or without food, i.e., substantially independent of food effect, to a human subject in need of such administration.

Thus, certain embodiments call for pharmaceutical compositions comprising at least one Omega-3 fatty acid ester and at least one surface active agent; wherein said at least one Omega-3 fatty acid ester comprises at least about 40% (wt/wt) of the composition.

Certain embodiments call for pharmaceutical compositions comprising a first Omega-3 fatty acid ester selected from the group consisting of hexadecatrienoic acid, α-linolenic acid, stearidonic acid, eicosatrienoic acid, eicosapentaenoic acid, heneicosapentaenoic acid, docosapentenoic acid, docosahexaenoic acid, tetracosapentenoic acid, tetracosahexaenoic acid, and a second Omega-3 fatty acid ester selected from the group consisting of hexadecatrienoic acid, α-linolenic acid, stearidonic acid, eicosatrienoic acid, eicosapentaenoic acid, heneicosapentaenoic acid, docosapentenoic acid, docosahexaenoic acid, tetracosapentenoic acid, tetracosahexaenoic, such that the first and second Omega-3 fatty acid esters selected are different from each other and the ratio of the first and second Omega-3 fatty acid esters are in a ratio of more than 2:1 to not more than 3.4:1 (first Omega-3 fatty acid ester:second Omega-3 fatty acid ester); wherein the first and second Omega-3 fatty acid esters combined comprise at least about 40% (wt/wt) of the composition and wherein said composition is substantially free of active ingredients other than said Omega-3 fatty acid esters.

Certain embodiments call for the use of at least one Omega-3 fatty acid ester. Typically, the Omega-3 fatty acid ester is an ethyl ester.

Certain embodiments call for pharmaceutical compositions comprising at least one Omega-3 fatty acid ester and at least one terpene; wherein said at least one Omega-3 fatty acid ester comprises at least about 40% (wt/wt) of the composition and is substantially free of active ingredients other than Omega-3 fatty acid esters. In certain embodiments, the at least one Omega-3 fatty acid ester comprises about 40%, 45%, 50%, 55%, 60%, 65%, 70%, 75%. The terpene is typically, but not necessarily d-limonene. In certain other embodiments, such compositions comprise natural orange-oil.

Certain embodiments provide for compositions comprising EPA ethyl esters and DHA ethyl esters and at least one terpene, wherein the ratio of EPA:DHA is about 2.4:1 and wherein said EPA and DHA ethyl esters combined comprise from about 40% (wt/wt) to about 95% (wt/wt) of said composition. In certain embodiments, the EPA and DHA ethyl esters combined comprise about 40% (wt/wt) of said composition. The terpene is typically, but not necessarily d-limonene. In certain other embodiments, such compositions comprise natural orange-oil.

In embodiments comprising substantially pure d-limonene, the d-limonene is from about 95% to about 98% pure. In certain embodiments, the substantially pure d-limonene is at least 95%, 96%, 97% or 98% pure.

In certain embodiments, the Omega-3 fatty acid ester is selected from the group consisting of at least one EPA ester, at least one DHA ester or combinations thereof, and comprises at least one surface active agent. In certain embodiments, the at least one EPA ester and at least one DHA ester is substantially pure. Certain embodiments also provide for compositions comprising at least one EPA ester and at least one DHA ester in ratios from about 2:1 to about 3.4:1, which are substantially free of active ingredients other than Omega-3 fatty acid esters. Compositions comprising other ratios are also described. Certain compositions can also be free of natural orange oil or d-limonene. In certain embodiments, the Omega-3 fatty acid esters comprise at least 40% of the composition. Typically, the Omega-3 EPA and DHA esters are ethyl esters. Certain compositions described herein form micelles in an aqueous medium and are free of food effect. Certain compositions, when administered with or without food, are substantially free of food effect. Provided herein are also methods for treating cardiovascular conditions or disorders using the compositions described. The compositions described herein minimize or eliminate side effects when compared to the administration of prior art compositions. Also provided are packaged compositions or kits of the Omega-3 fatty acid esters comprising one or more unit dosage forms together with instructions on using the compositions.

Accordingly, in at least one embodiment is provided, a pharmaceutical composition comprising at least one EPA ester and at least one DHA ester in a weight to weight ratio of more than about 2:1 to not more than about 3.4:1 (EPA:DHA) and at least one surface active agent, wherein said EPA and DHA esters combined comprises from about 40% to about 85% by weight of the composition. In certain such embodiments, the EPA and DHA ethyl esters combined comprise about 50% (wt/wt) of said composition.

In at least one other embodiment is provided, a pharmaceutical composition comprising at least one EPA ester and at least one DHA ester in a weight to weight ratio from about 2:1 to about 3.4:1 (EPA:DHA) and at least one surface active agent, wherein said EPA and DHA esters combined comprises from about 40% to about 85% by weight of the composition. In certain such embodiments, the EPA and DHA ethyl esters combined comprise about 50% (wt/wt) of said composition.

In at least one other embodiment is provided, a pharmaceutical composition comprising at least one EPA ester and at least one DHA ester in a weight to weight ratio of more than 2:1 to not more than 3.4:1 (EPA:DHA) and at least one surface active agent, wherein said EPA and DHA esters combined comprises from about 40% to about 85% by weight of the composition. In certain such embodiments, the EPA and DHA ethyl esters combined comprise about 50% (wt/wt) of said composition.

In at least one other embodiment is provided, a pharmaceutical composition comprising at least one EPA ester and at least one DHA ester in a weight to weight ratio of more than 2:1 to not more than 3.4:1 (EPA:DHA) and at least one surface active agent, wherein said EPA and DHA esters combined comprises from about 40% to about 85% by weight of the composition, and wherein the composition when administered with or without food to a human subject in need of such administration is substantially independent of food effect. In certain such embodiments, the EPA and DHA ethyl esters combined comprise about 50% (wt/wt) of said composition.

In at least one embodiment, the compositions described herein comprise substantially pure at least one EPA ester and/or at least one DHA ester.

In at least one embodiment, the compositions described herein consist essentially of the at least one EPA ester and/or the at least one DHA ester.

In certain embodiments, either of, or each of, the EPA and DHA ester comprising the composition is the ethyl ester.

In certain embodiments, the compositions described herein comprise substantially pure EPA ethyl ester and/or substantially pure DHA ethyl ester.

In certain embodiments, the compositions described herein consist essentially of substantially pure EPA ethyl ester and/or substantially pure DHA ethyl ester.

In certain embodiments, the ratio of the EPA and DHA ester comprising the composition is about 2.4:1 (EPA ester: DHA ester).

Certain embodiments call for compositions comprising either natural orange oil from about 0.1% to about 5% (wt/wt) of said composition. In embodiments comprising natural orange oil the natural orange oil is present at about 1.6% (wt/wt) of the composition. Certain other embodiments comprise substantially pure d-limonene from about 0.1% to about 5%. In embodiments comprising substantially pure d-limonene, the d-limonene is present at about 1.5% (wt/wt) of the composition.

In certain embodiments, the pharmacologic effect of the compositions described herein is substantially independent of a food effect upon administration to a subject.

In at least one embodiment, a pharmaceutical mixed-fatty-acids composition in which, a) at least 80% by weight of the composition is comprised of a combination of (all-omega-3)-5,8,11,14,17-eicosapentaenoic acids (EPA) and (all-Z omega-3)-4,7,10,13,16,19-docosahexaenoic acids (DHA) in a weight ratio of EPA:DHA of from about 1:2 to about 2:1; b) (all-Z omega-3)-6,9,12,15,18-heneicosapentaenoic acid is present in an amount of at least one percent by weight; and c) at least one surface active agent is provided. These compositions can optionally further comprise natural orange oil from about 0.1% to about 5% (wt/wt) or substantially pure d-limonene from about 0.1% to about 5% (wt/wt) of the composition. The natural orange oil is typically present at about 1.6% (wt/wt) of said composition and d-limonene is typically present at about 1.5% (wt/wt) of the composition.

In at least one embodiment, a mixed-fatty-acids composition for the treatment or prophylaxis of at least one of the multiple risk factors for CVD in which, a) at least 80% by weight of the composition is comprised of Omega-3 fatty acids; b) at least 80% by weight of the total fatty acid content of the composition is comprised of a combination of (all-Z omega-3)-5,8,11,14,17-eicosapentaenoic acid (EPA) and (all-Z omega-3)-4,7,10,13,16,19-docosahexaenoic acid (DHA) in a weight ratio of EPA:DHA of from 1:2 to 2:1, c) Omega-3 fatty acids other than EPA and DHA are present in an amount of at least 1.5% by weight of the total fatty acids; and c) at least one surface active agent is provided. These compositions can optionally further comprise natural orange oil from about 0.1% to about 5% (wt/wt) or substantially pure d-limonene from about 0.1% to about 5% (wt/wt) of the composition. The natural orange oil is typically present at about 1.6% (wt/wt) of said composition and d-limonene is typically present at about 1.5% (wt/wt) of the composition.

In at least one embodiment a pharmaceutical mixed-fatty-acids composition in which, a) at least 80% by weight of the composition is comprised of a combination of (all-omega-3)-5,8,11,14,17-eicosapentaenoic acid (EPA) and (all-Z omega-3)-4,7,10,13,16,19-docosahexaenoic acid (DHA) in a weight ratio of EPA:DHA of from 1:2 to 2:1, b) at least 3% by weight of the composition is comprised of Omega-3 fatty acids other than EPA and DHA that have 18, 20, 21, or 22 carbon atoms, and c) at least one surface active agent is provided. These compositions can optionally further comprise natural orange oil from about 0.1% to about 5% (wt/wt) or substantially pure d-limonene from about 0.1% to about 5% (wt/wt) of the composition. The natural orange oil is typically present at about 1.6% (wt/wt) of said composition and d-limonene is typically present at about 1.5% (wt/wt) of the composition.

In at least one embodiment, a pharmaceutical mixed-fatty-acids composition in which, a) at least 90% by weight of the composition is comprised of long chain, polyunsaturated, Omega-3 fatty acids; b) at least 80% by weight of the composition is comprised of a combination of (all-Z omega-3)-5,8,11,14,17-eicosapentaenoic acid (EPA) and (all-Z omega-3)-4,7,10,13,16,19-docosahexaenoic acid (DHA) in a weight ratio of EPA:DHA of from 1:1 to 2:1, with the EPA constituting 40 to 60% by weight of the composition and the DHA constituting 25 to 45% by weight of the composition; c) at least 4.5% by weight of the composition is comprised of Omega-3 fatty acids other than EPA and DHA that have 18, 20, 21, or 22 carbon atoms; d) from 1 to 4% by weight of the composition is comprised of (all-Z omega-3)-6,9,12,15,18-heneicosapentaenoic acid; e) at least one surface active agent; and f) the composition is in oral dosage form and includes an effective amount of a pharmaceutically acceptable antioxidant. These compositions can optionally further comprise natural orange oil from about 0.1% to about 5% (wt/wt) or substantially pure d-limonene from about 0.1% to about 5% (wt/wt) of the composition. The natural orange oil is typically present at about 1.6% (wt/wt) of said composition and d-limonene is typically present at about 1.5% (wt/wt) of the composition.

It should be noted that in all of the embodiments comprising compositions described herein, the total of all ingredients comprising the composition does not exceed 100%.

In certain embodiments is provided, a pharmaceutical or drug composition comprising EPA and DHA in a weight to weight ratio of about 3.5:1 to about 5:1 and at least one surface active agent, and wherein the composition is more than 84% combined EPA and DHA by weight. These compositions can optionally further comprise natural orange oil from about 0.1% to about 5% (wt/wt) or substantially pure d-limonene from about 0.1% to about 5% (wt/wt) of the composition. The natural orange oil is typically present at about 1.6% (wt/wt) of said composition and d-limonene is typically present at about 1.5% (wt/wt) of the composition.

Certain embodiments provide for certain compositions comprising at least about 96% by weight, ethyl eicosapentaenoate (ethyl-EPA), at least one surface active agent, substantially no docosahexaenoic acid (DHA) or its esters. These compositions can optionally further comprise natural orange oil from about 0.1% to about 5% (wt/wt) or substantially pure d-limonene from about 0.1% to about 5% (wt/wt) of the composition. The natural orange oil is typically present at about 1.6% (wt/wt) of said composition and d-limonene is typically present at about 1.5% (wt/wt) of the composition.

In at least one embodiment, a method is provided for treating the following disorders: metabolic syndrome, macular degeneration, Omega-3 deficiency, cognitive impairment, including as a result of surgery or traumatic brain injury (such as, for example, resulting from a concussion), major depression, suicide, post-partum depression, inflammation, primary sclerosing cholangitis, borderline personality disorder in women, breast cancer, non-alcoholic fatty acid liver disease, and improvement in cognition and behavior in children. These conditions or disorders can be treated by administering the compositions described herein to a subject, typically a human, in need of such administration.

In at least one embodiment, a method is provided for treating at least one cardiovascular condition or disorder in a subject in need of such treatment, said method comprising administering to a subject at least one composition described herein comprising a therapeutically effective amount of the Omega-3 fatty acid esters and at least one surface active agent.

In at least one embodiment a method is provided for treating at least one cardiovascular condition or disorder, for example and without limitation disorders of the heart and vasculature, including, for example, hypertension, hyperlipidemia, hypertriglyceridemia, atherosclerosis, transient ischemic attack, systolic dysfunction, diastolic dysfunction, aneurysm, aortic dissection, myocardial ischemia, acute myocardial infarction (AMI), acute ST-segment elevation myocardial infarction (STEMI), acute non-ST-segment elevation myocardial infarction (NSTEMI), angina pectoris, unstable angina (UA), and stable angina (SA), myocardial infarction, congestive heart failure, dilated congestive cardiomyopathy, hypertrophic cardiomyopathy, restrictive cardiomyopathy, corpulmonale, arrhythmia, valvular heart disease, endocarditis, pulmonary embolism, venous thrombosis, peripheral vascular disease, and peripheral artery disease. The method comprises administering to a subject in need of treatment a therapeutically effective amount of a composition described herein.

In at least one embodiment, a method is provided for treating hypertension and/or hyperlipidemia.

In at least one other embodiment, a method is provided for treating hypertriglyceridemia.

In certain embodiments, the total amount of triglycerides (TG) in a human subject's blood having ≥150 mg TG per dL of serum at the start of the dosing regimen is reduced by at least 20% within about 30 days following administration of certain embodiments of the compositions described herein.

In at least one other embodiment, a method is provided for treating a human subject having ≥150 mg TG per dL of serum who is in need of such treatment, said method comprising administering to the human subject at least one embodiment of the composition described herein comprising a therapeutically effective amount of Omega-3 fatty acid esters.

Embodiments are also provided wherein the compositions described herein are packaged together as a kit with instructions on how to use the compositions for treating cardiovascular conditions or disorders.

In certain embodiments, the surface active agent is selected from the group consisting of at least one nonionic surface active agents, cationic surface active agents, anionic surface active agents, zwitterionic surface active agents, or combinations thereof In certain embodiments, the surface active agent is selected from the group consisting of at least one anionic surface active agent, at least one non-ionic surface active agent, and a combination thereof.

In certain embodiments comprising at least one surface active agent, the at least one surface active agent has a hydrophilic-lipophilic balance (HLB) of about 8.0.

In certain embodiments comprising at least one surface active agent, the surface active agent can be a non-ionic surface active agent selected from the group consisting of at least one polysorbate, at least one poloxamer, and a combination thereof.

In certain embodiments, the at least one surface active agent comprises a polysorbate present from about 15% wt/wt to about 31% wt/wt of the composition. In certain embodiments, the polysorbate is polysorbate 80.

In certain other embodiments, the at least one surface active agent comprises a poloxamer present from about 0.1% to about 5% wt/wt of the composition.

In certain embodiments, the compositions described herein comprise a combination of polysorbate 80 and the poloxamer PLURONIC® F87 [(HO($C_2H_4O$)$_{64}$($C_3H_6O$)$_{37}$($C_2H_4O$)$_{64}$H].

In certain embodiments, the composition further comprises at least one antioxidant. In such embodiments the at least one antioxidant is selected from the group consisting of a tocopherol, a tocotrienol, or combinations thereof. In such embodiments, the tocopherol, tocotrienol or combinations thereof is present from about 0.01% to about 5% by weight of the compositions. In certain such embodiments, the tocopherols, tocotrienols or combinations thereof can be present at about 0.01%, 0.05%, 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5% or 5% by weight of the compositions. In certain such embodiments, the tocopherols, tocotrienols, or combinations thereof can be present at about 0.4% by weight of the compositions. In certain embodiments, the tocopherol, tocotrienol or combinations is present at about 0.4% by weight of the composition. In certain embodiments further comprising at least one antioxidant, the antioxidant is a tocopherol at about 0.4% by weight of the composition.

In certain embodiments, the composition self-micellizes in an aqueous medium. In certain other embodiments, the aqueous medium is water. In certain other embodiments, the aqueous medium has an acidic pH. In certain other embodiments, the aqueous medium is 0.1N HCl.

In certain embodiments, the compositions described herein self-micellizes in an aqueous medium wherein the micelles have a diameter from about 1 μm to about 10 μm. In certain embodiments, the compositions described herein self-micellizes in an aqueous medium having an acidic pH, wherein the micelles have a diameter from about 1 μm to about 10 μm. In certain other embodiments, the compositions described herein self-micellizes in 0.1N HCL, wherein the micelles have a diameter from about 1 μm to about 10 μm. In certain embodiments, the micelles have an average diameter of about 1, 2, 3, 4, 5, 6, 7, 8, 9, or 10 μm.

In certain embodiments, the compositions described herein can be administered with or without food to a human subject in need of such administration wherein the bioavailability of the Omega-3 fatty acid esters comprising the compositions are substantially independent of food effect.

Certain embodiments provide for compositions that minimize or eliminate at least one side effect from the administration of a composition of the present disclosure when compared to the administration of a composition comprising Omega-3 fatty acid esters substantially free of a surface active agent. In other embodiments, non-limiting examples of the side effects include regurgitation, frequency of burping, gastroesophageal reflux disease (GERD), bloating, increased intestinal gas, fish taste, fishy breath, fish smell, nausea, diarrhea, or combinations thereof.

In certain embodiments, the compositions described herein comprise d-limonene or natural orange oil. Such compositions can minimize or eliminate at least one side effect from the administration of a composition of the present disclosure when compared to the administration of a composition comprising Omega-3 fatty acid esters substantially free of d-limonene or natural orange oil. In other embodiments, non-limiting examples of the side effects include regurgitation, frequency of burping, gastroesophageal reflux disease (GERD), bloating, increased intestinal gas, fish taste, fishy breath, fish smell, nausea, diarrhea, or combinations thereof.

In certain embodiments, the compositions described herein when administered to a human subject selected from the group consisting of individuals having from about 155 to about 199 mg TG per dL of serum, from about 200 to about 499 mg TG per dL of serum and from about 500 mg or higher TG per dL of serum, lowers said subject's serum TG levels by at least about 20%.

Certain embodiments of the compositions described herein can be administered to a human subject in need of such administration with a non-Omega-3 fatty acid ester lipid-lowering agent selected from the group consisting of cholesterol absorption inhibitors, bile acid sequestrants/resins, statins, niacin and derivatives, MTP inhibitors, fibrates and CETP inhibitors.

In certain embodiments, the compositions described herein can reduce the total amount of TG in the serum of a human subject being treated for hypertriglyceridemia by at least about 20% within about 30 days of administration of the composition wherein the human subject's blood measures≥150 mg TG per dL of serum at the start of the dosing regimen.

In at least one embodiment, the compositions described herein can be administered orally or parenterally in a suitable dosage form. When administered orally, the compositions described herein can be administered, typically, but not necessarily, in the form of a gel or liquid capsule.

In certain other embodiments, methods are provided for administering at least about 0.5 g/day of certain embodiments of the compositions described herein comprising from about 40% to about 85% by weight of the composition, at least one EPA ester and at least one DHA ester in a ratio of more than 2:1 to not more than 3.4:1 and at least one surface active agent. Typically, but not necessarily, the ester is an ethyl ester and the at least one surface active agent is polysorbate 80, PLURONIC® F87 or a combination thereof. In certain such embodiments, the EPA and DHA ethyl esters combined comprise about 50% (wt/wt) of said composition. Optionally, the composition can further comprise substantially pure d-limonene or natural orange oil.

In certain other embodiments, methods are provided for administering at least about 4 g/day of certain embodiments of the compositions described herein comprising ethyl eicosapentaenoic acid (ethyl-EPA), at least one surface active agent and substantially no docosahexaenoic acid (DHA), where the ethyl-EPA constitutes at least about 96% by weight of the total Omega-3 fatty acid esters in the composition. In certain embodiments, such compositions can further comprise natural orange oil or substantially pure d-limonene.

Certain embodiments provide for the use of the compositions described herein in the manufacture of a medicament for the treatment of a cardiovascular disease or disorder. In certain embodiments, the cardiovascular disease or disorder is hyperlipidemia. In certain other embodiments, the cardiovascular disease or disorder is hypercholesterolemia. In certain embodiments, the cardiovascular disease or disorder is hypertriglyceridemia.

Certain embodiments provide for the use of the compositions described herein in the manufacture of a medicament for the treatment of a cardiovascular disease or disorder. In certain embodiments, the cardiovascular disease or disorder is hyperlipidemia. In certain other embodiments, the cardiovascular disease or disorder is hypercholesterolemia. In certain embodiments, the cardiovascular disease or disorder is hypertriglyceridemia.

In certain embodiments, administration of the compositions described herein provide for a blood serum concentration in a human subject of at least about 20 nmol/mL of combined at least one EPA ester and at least one DHA ester within about four hours after administration of the certain embodiments.

Also provided are kits comprising compositions of the Omega-3 fatty acid esters as one or more unit dosage forms together with instructions on using the dosage forms. In certain embodiments, the dosage forms described herein can be packaged as blister packs or in bottles with instructions for using the dosage forms. For example, the instructions can be provided as a package insert or directly on a label attached to the blister pack, bottle or on secondary packaging in which the blister pack or bottle was provided to a human subject. The instructions can include, for example, dosing frequency, administration of the dosage forms with or without food, the active ingredients comprising the dosage forms, and the cardiovascular conditions or disorders that would benefit from administration of the dosage forms.

In certain embodiments kits are provided, wherein certain dosage forms comprising the compositions described herein can be packaged together with other non-Omega-3 fatty acid ester lipid lowering agents. The kit(s) comprise one or more unit dosage forms of certain embodiments of the compositions described herein together with one or more unit dosage forms comprising the non-Omega-3 fatty acid ester lipid-lowering agents together with instructions on using the dosage forms.

Certain embodiments provide for a functional food(s) for treating and/or preventing CVD comprising the compositions described herein.

Certain embodiments provide methods of treating CVD by administering a functional food comprising the compositions described herein.

Certain embodiments provide for a functional food(s) comprising the compositions described herein, and methods to treat hypertriglyceridemia in a human subject.

DETAILED DESCRIPTION

Figure 1:
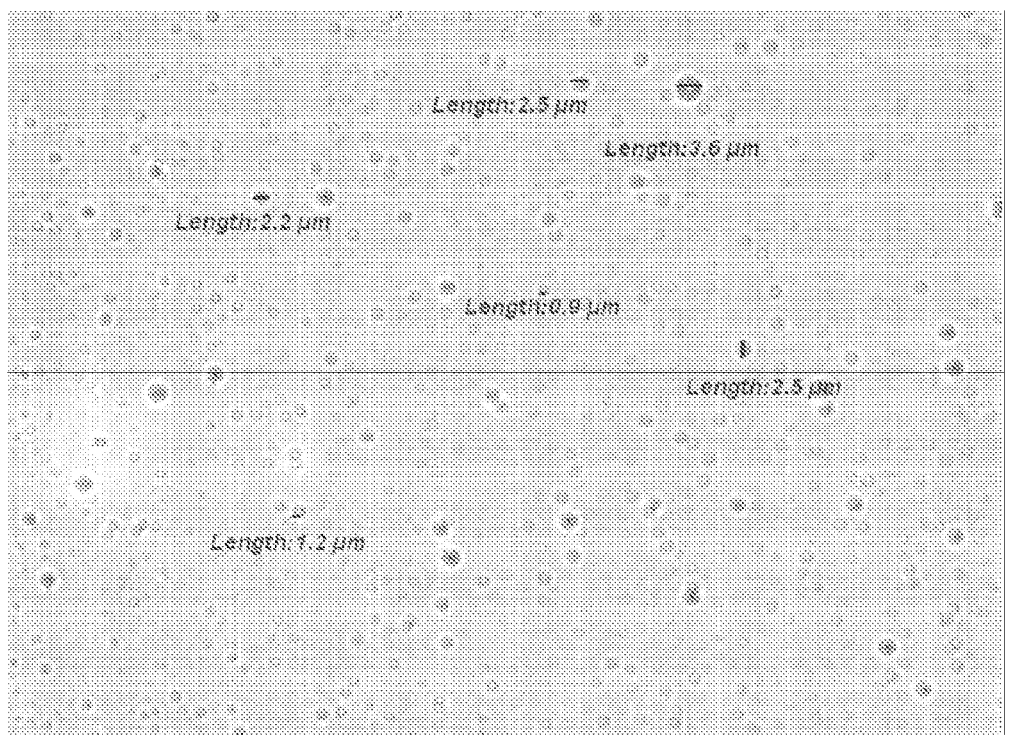
FIG. 1 depicts a photomicrograph of an embodiment. A composition comprising micelles, as described herein, was prepared, added between a slide and cover slip, observed at 40× magnification with a Nikon Model Trinocular Head and a Spot RT3 digital camera, and the diameters of several representative micelles were measured.
Figure 2:
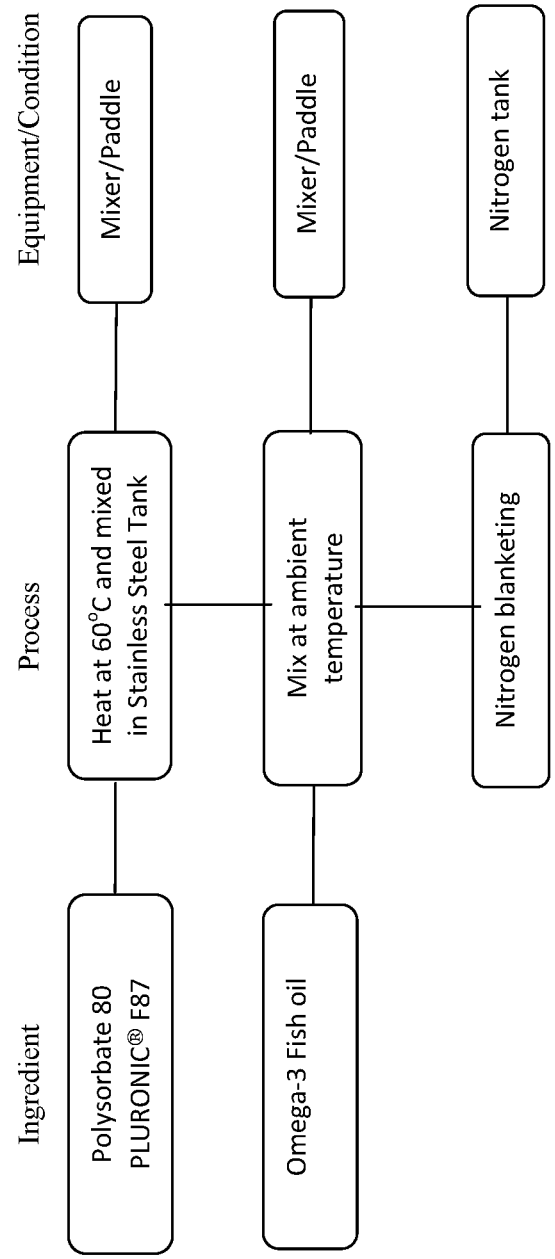
FIG. 2 shows a schematic flowchart of the process for manufacturing one embodiment of the compositions described herein.
Figure 3:
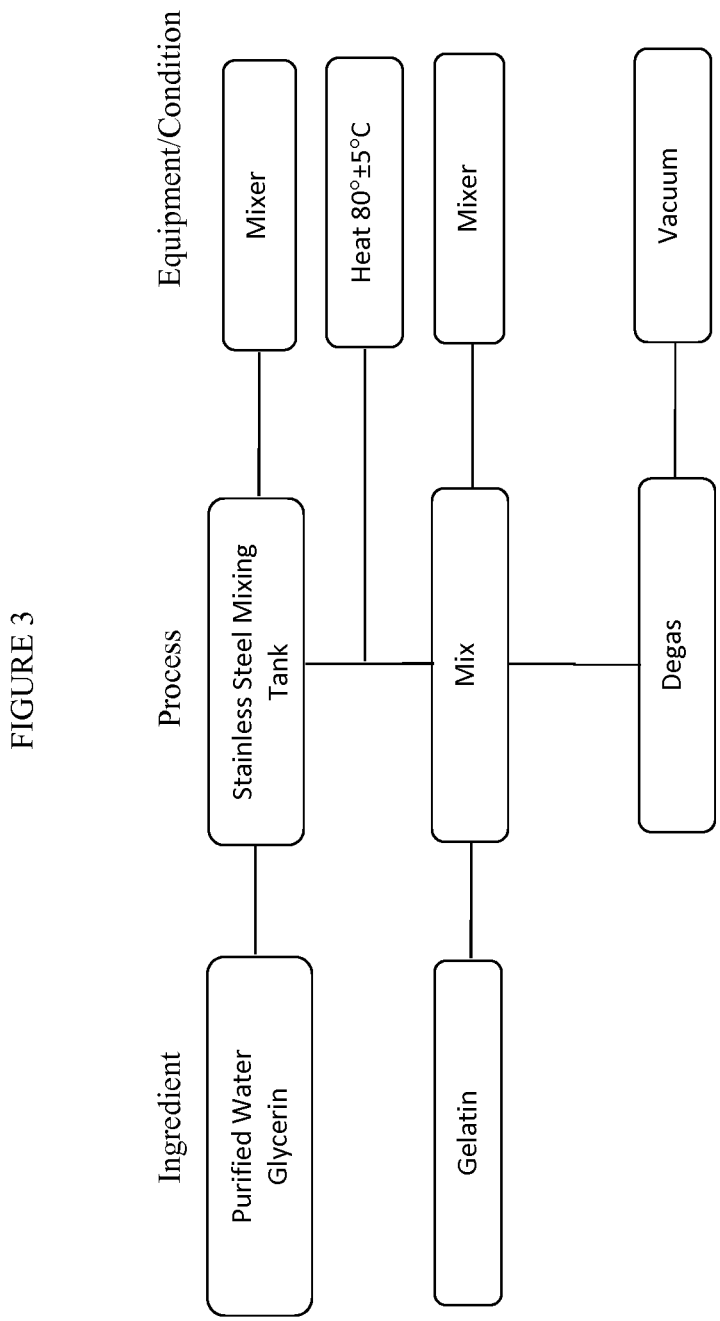
FIG. 3 shows a schematic flowchart of the process for manufacturing the gel mass for encapsulating one embodiment of the compositions described herein.
Figure 4:
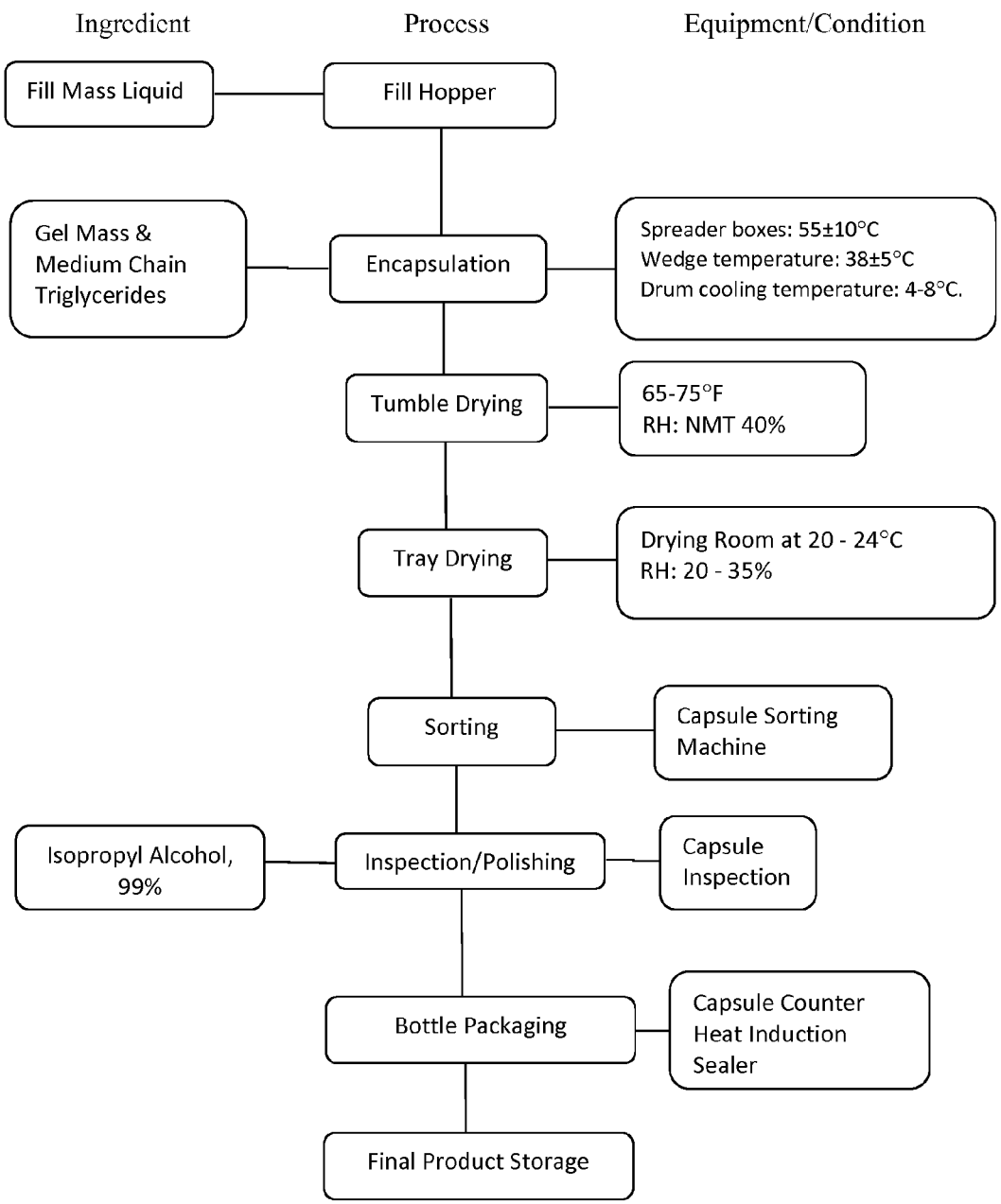
FIG. 4 shows the a schematic flowchart of the encapsulation process for manufacturing one dosage form comprising one embodiment of the compositions described herein.

Certain aspects, modes, embodiments, variations and features of the invention are described herein in various levels of detail to provide further understanding of embodiments related to compositions comprising Omega-3 fatty acid esters, and methods related to using such compositions containing a high concentration of Omega-3 fatty acid esters. In certain embodiments, an EPA ester and DHA ester are present in specific weight ratio percentages and relative amounts. As noted, these compositions have beneficial effects on certain risk factors for CVD, including the lowering of serum triglycerides and serum cholesterol.

DEFINITIONS

As used herein, the term "composition(s)" or "formulation(s)" includes therapeutic and dietary compositions including, but not limited to a dietary supplement, nutraceutical formulation, or pharmaceutical formulation. Further, the terms composition, dietary supplement, nutraceutical formulation, and pharmaceutical formulation are used interchangeably herein.

As used herein, the term "EPA" refers inclusively to (5Z,8Z,11Z,14Z,17Z)-eicosa-5,8,11,14,17-pentenoic acid or derivatives thereof, including alkyl esters, such as, for example, the ethyl ester.

As used herein, the term "DHA" inclusively refers to (4Z,7Z,10Z,13Z,16Z,19Z)-docosa-4,7,10,13,16,19-hexaenoic acid or derivatives thereof, including alkyl esters, such as, for example, the ethyl ester.

As used herein, the term "micelle" (plural micelles, micella, or micellae) refers to an aggregate of molecules, that have assembled into an approximately spherical core/shell architecture, and are suspended in an aqueous phase. A typical micelle in aqueous solution forms an aggregate with the hydrophilic "head" regions in contact with surrounding solvent and/or in contact with the polar region of one or more surface active agent(s), sequestering the hydrophobic regions in the micelle center. Micelles are approximately spherical in shape.

The term "self-micellizes" as used herein refers to the process in which micelles are formed in an aqueous medium without the introduction of energy, including agitation or shearing.

As used herein, the term "aqueous medium" refers to any solution or suspension, that comprises water, including for example, without limitation, water by itself; phosphate buffered saline pH 7.4, Sprite, apple juice, G-2 fruit punch, and chocolate milk. In certain embodiments, an aqueous medium comprises at least one fluid having an acidic pH. In certain other embodiments, an aqueous medium comprises a biological fluid such as, for example and without limitation, stomach acid. In other embodiments, the aqueous medium comprises simulated stomach acid comprising 0.1N HCl.

As used herein, the term "free fatty acid" refers to one or more polyunsaturated fatty acids that have not been modified or do not have any other groups attached.

As used herein, the term "ester" refers to the replacement of the hydrogen in the carboxylic acid group of a polyunsaturated fatty acid molecule with another substituent. Typical esters are known to those in the art, a discussion of which is provided by Higuchi, T. et al., *Pro-drugs as Novel Delivery Systems*, Vol. 14, A.C.S. Symposium Series, *Bioreversible Carriers in Drug Design*, Ed. Edward B. Roche, Amer. Pharma. Assoc., Pergamon Press (1987), and *Protective Groups in Organic Chemistry*, McOmie ed., Plenum Press, New York (1973), each of which is incorporated herein by reference in the entirety. Examples of common esters include methyl, ethyl, trichloroethyl, propyl, butyl, pentyl, tert-butyl, benzyl, nitrobenzyl, methoxybenzyl, benzhydryl, monoglyceride, diglyceride, triglyceride.

As used herein, the term "monoglyceride" refers to a fatty acid chain, such as DHA or EPA molecule, covalently bonded to a glycerol molecule through an ester linkage. As used herein, the term "diglyceride" refers to a fatty acid chain such as DHA or EPA, covalently bonded to a glycerol molecule through an ester linkage, wherein the glycerol molecule is further bonded to one additional fatty acid chain, which may or may not be DHA or EPA, through one additional ester linkage. As used herein, the term "triglyceride" refers to a fatty acid chain, such as DHA or EPA, covalently bonded to a glycerol molecule through an ester linkage, wherein the glycerol molecule is further bonded to two additional fatty acid chains, either or both of which may or may not be DHA or EPA, through two additional ester linkages.

As used herein, the term "terpene" refers to the large and diverse class of organic compounds produced by a variety of plants, particularly conifers. When terpenes are modified chemically, such as by oxidation or rearrangement of the carbon skeleton, the resulting compounds are generally referred to as "terpenoids" (e.g., carvone). Terpenes and terpenoids are the primary constituents of the essential oils of many types of plants and flowers.

As used herein, the terms "α-Tocopherol," "tocopherol," and "vitamin E" each refer to a set of tocopherols and tocotrienols, which are fat-soluble vitamins with antioxidant properties.

As used herein, the term "antioxidant" refers to a molecule capable of inhibiting the oxidation of other molecules. Oxidation is a chemical reaction that transfers electrons or hydrogen from a substance to an oxidizing agent. Oxidation reactions can produce free radicals. In turn, these radicals can start chain reactions. When the chain reaction occurs in a cell, it can cause damage or death to the cell. Antioxidants terminate these chain reactions by removing free radical intermediates, and inhibit other oxidation reactions. They do this by being oxidized themselves, so antioxidants are often reducing agents such as thiols, ascorbic acid, or polyphenols. Exemplary antioxidants include rosemary oil, ascorbic acid (vitamin C), glutathione, lipoic acid, uric acid, carotenes, melatonin, ubiquinol (coenzyme Q), α-tocopherol (vitamin E), acorbyl palmitate, butylated hydroxy anisole, butylated hydroxytoluene, monothioglycerol, and potassium metabisulfite.

As used herein, a pharmaceutically acceptable "carrier" refers to any substance suitable as a vehicle for delivering a molecule or composition to a suitable in vivo site of absorption. Examples of such carriers include, but are not limited to water, phosphate buffered saline (PBS), Ringer's solution, dextrose solution, serum-containing solutions, Hank's solution and other aqueous physiologically-balanced solutions.

As used herein, a pharmaceutically acceptable "preservative" includes but is not limited to potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

As used herein, a "coloring agent" provides coloration to the composition or dosage form. Such coloring agents include food grade dyes.

As used herein, the term "subject" refers to a mammal, including but not limited to a dog, cat, horse, cow, pig, sheep, goat, chicken, rodent, primate or human. Subjects include animals such as house pets (e.g., dogs, cats, and the like), agricultural stock subjects (e.g., cows, horses, pigs, chickens, etc.), laboratory subjects (e.g., mice, rats, rabbits, etc.), but are not so limited. The human subject may be a pediatric, adult, or a geriatric subject. The human subject may be of either gender.

As used herein, the terms "cardiovascular disease" and "cardiovascular condition" include disorders of the heart and vasculature, including, for example, hypertension, hyperlipidemia, hypertriglyceridemia, atherosclerosis, transient ischemic attack, systolic dysfunction, diastolic dysfunction, aneurysm, aortic dissection, myocardial ischemia, acute myocardial infarction (AMI), acute ST-segment elevation myocardial infarction (STEMI), acute non-ST-segment elevation myocardial infarction (NSTEMI), angina pectoris, unstable angina (UA), and stable angina (SA), myocardial infarction, congestive heart failure, dilated congestive cardiomyopathy, hypertrophic cardiomyopathy, restrictive cardiomyopathy, corpulmonale, arrhythmia, valvular heart disease, endocarditis, pulmonary embolism, venous thrombosis, peripheral vascular disease, and peripheral artery disease.

Hypertriglyceridemia, for example, is a condition related to cardiovascular disease in which fasting blood serum concentrations of triglycerides are ≥150 mg/dL. Blood concentrations can rise from moderately high levels of 200 mg/dL to 500 mg/dL, or in severe cases, above 500 mg/dL. The American Heart Association has categorized triglyceride concentrations as "normal" (below 150 mg/dL), "elevated" (150 to 199 mg/dL), "high" (200 to 499 mg/dL), and "very high" (above 500 mg/dL). It will be evident to the skilled practitioner that the categorization of hypertriglyceridemia can vary from country to country. For example, Canadian and European guidelines recommend fasting blood serum triglyceride levels of less than 1.7 mmol/L as "desirable", from 1.7 to 2.2 mmol/L as "borderline high" and 2.3 to 5.6 mmol/L as "high" and above 5.6 mmol/L as "very high". The skilled practitioner will also appreciate that what constitutes elevated blood serum triglyceride levels may vary based on age and gender.

As used herein, an "effective amount" or "therapeutically effective amount" of a composition as described in some embodiments herein can be a quantity sufficient to achieve a desired therapeutic and/or prophylactic effect, for example, an amount which results in the prevention of, or a decrease in the symptoms associated with, a disease that is being treated. The amount of composition administered to the subject, particularly one in need of the composition, can depend on the type and severity of the disease and on the characteristics of the individual, such as general health, age, sex, body weight and tolerance to drugs. A person skilled in the art will be able to determine appropriate dosages depending on these and other factors. Typically, an effective amount of the compositions described herein can be sufficient for achieving a therapeutic or prophylactic effect.

The terms "dose unit," "unit dose," and "dosage unit," as used herein, refer to a portion of a composition that contains an effective amount of an active suitable for a single administration to provide, or contribute to, a therapeutic effect. Such dosage units may be administered one to a plurality (i.e., 1 to about 10, 1 to 8, 1 to 6, 1 to 4 or 1 to 2) of times per day, or as many times as needed to elicit a therapeutic response.

The term "food effect," as used herein, refers to a relative difference in AUC (area under the curve), $C_{max}$ (maximum plasma concentration), and/or $T_{max}$ (time to maximum concentration) of an active substance, when said substance or a composition thereof, such as a tablet, a capsule or a liquid, is administered orally to a subject concomitantly with food or in a fed state as compared to the same values when the same composition is administered in a fasted state. The food effect, F, is calculated as:

$$F = (Y_{fed} - Y_{fasted})/Y_{fasted}$$

wherein $Y_{fed}$ and $Y_{fasted}$ are the found values of AUC, $C_{max}$, or $T_{max}$ in the fed and fasted state, respectively. A food effect, F, is generally established when F>1.

In general, the term "AUC" or "area under the plasma concentration-time curve" is related to the total amount of an active measurable in the systemic circulation following administration of a single dose. The AUC is a mathematical and visual representation of the aggregate amount of the active in the systemic circulation over a given period of time. Changes in the AUC need not necessarily reflect changes in the total amount of the active absorbed but can reflect modifications in the kinetics of distribution, metabolism and excretion. Accordingly, the term AUC as used herein refers to the total amount of Omega-3 fatty acids measurable in the systemic circulation following administration of a single dose of any of the compositions described herein.

The term "$T_{max}$" or "time of peak concentration" refers to the period of time required to achieve peak plasma concentration of an active after administration of a single dose. Accordingly, the term $T_{max}$ as used herein refers to the period of time required to achieve peak plasma concentration of Omega-3 fatty acid esters after administration of a single dose of any of the compositions described herein.

The term "$C_{max}$" or "peak concentration" is the highest concentration of an active achieved in the blood plasma. Accordingly, the term $C_{max}$ as used herein refers to the maximum concentration of Omega-3 fatty acid esters after administration of a single dose of any of the compositions described herein.

The term "substantially independent of a food effect," or "substantially free of food effect" as used herein, refers to a substantial elimination of the effect of food upon the absorption (e.g., F is about 0), following oral administration, of any of the compositions described herein. In other words, the bioavailability of the Omega-3 fatty acid esters, as measured by the logarithm-transformed AUC, is substantially the same regardless of whether the compositions described herein are administered with or without food. In certain embodiments, the pharmacological effects of administration of compositions described herein are substantially independent of a food effect.

The term "reduced food effect," as used herein, as used herein, refers to a substantial reduction in the effect of food upon the absorption, following oral administration, of any of the compositions described. In certain embodiments, the compositions described herein have a reduced food effect.

The term "concomitantly with food" or "administration in the fed state," as used herein, refers to administration from about 30 minutes before a meal to about 1 hour after a meal.

Various modes of treatment or prevention of medical conditions as described herein are intended to mean "substantial" or "substantially", which includes total but also less than total treatment or prevention, and wherein some biologically or medically relevant result is achieved. A subject, such as a human subject, in need of treatment refers to a subject in need of treatment of a defined disease state or in need of preventative treatment (i.e., prophylaxis) of such a disease state.

The term "about" or "approximately" as used herein means within an acceptable error range for the particular value as determined by one of ordinary skill in the art, which will depend in part on how the value is measured or determined, i.e., the limitations of the measurement system. Where particular values are described in the application and claims, unless otherwise stated, the term "about" means within an acceptable error range for the particular value.

The term "active(s)", "active ingredient(s)", "active agents" or "pharmaceutically active ingredient" means a chemical entity intended to furnish pharmacological activity or to otherwise have direct effect in the diagnosis, cure, mitigation, treatment or prevention of disease, or to have direct effect in restoring, correcting or modifying physiological functions in a subject.

The term "functional food" as used herein means any edible or drinkable foods or dietary components (e.g., juices, milk, yogurt, butter, margarine, baking products) that are fortified or enhanced with any of the compositions described herein. The functional food can be, e.g., solid, liquid, semi-solid, or a combination thereof. The term "functional food" also encompasses edible and drinkable nutritional supplements.

The term "hydrophilic-lipophilic balance" or "HLB," as used herein, refers to the relative affinity of a substance or composition for aqueous and oily phases. HLB values can be calculated based on methods and equations known to those of ordinary skill in the art, such as those described in U.S. Pat. No. 5,585,192. Substances or compositions generally have an average HLB of about 6 to about 20. Hydrophilic-lipophilic balance values can be determined in a variety of the formulas or experimental methods provided, for example, in U.S. Pat. No. 5,585,192.

The term "substantially pure" as used herein means at least 90% pure.

Pharmaceutical Compositions

In at least one embodiment, a composition is provided, wherein the composition comprises at least one Omega-3 fatty acid ester, at least one surface active agent, and wherein the composition self-micellizes when in contact with an aqueous medium. In certain embodiments, said at least one Omega-3 fatty acid ester comprises from about 40% (wt/wt) to about 85% (wt/wt) of the composition. In certain embodiments, the at least one Omega-3 fatty acid ester comprises about 40%, 45%, 50%, 55%, 60%, 65%, 70%, 75%, 80% or 85% (wt/wt) of the composition.

In certain embodiments, the compositions described herein self-micellize in 0.1N HCl. It is well accepted that 0.1N HCl (simulated gastric fluid), serves as a proxy for the acidity of stomach contents. Accordingly, and without being bound by theory, it is believed that the compositions described herein can self-micellize in situ in the stomach or small intestine. In certain embodiments, the compositions described herein more efficiently and effectively deliver Omega-3 fatty acid esters through the intestinal tract when administered with or without food.

Certain embodiments call for the use of Omega-3 fatty acid esters. Accordingly, in one aspect, a composition is provided comprising at least one (5Z,8Z,11Z,14Z,17Z)-eicosa-5,8,11,14,17-pentenoic acid (EPA) ester; or at least one (4Z,7Z,10Z,13Z,16Z,19Z)-docosa-4,7,10,13,16,19-hexaenoic acid (DHA) ester; or a combination thereof, wherein the composition has a ratio of EPA ester to DHA ester of more than 2.0:1.0 to not more than 3.4:1.0 and is substantially free of active ingredients other than said Omega-3 fatty acid esters. In certain embodiments, the Omega-3 fatty acid esters in said composition comprise Omega-3 fatty acid ethyl esters. In certain embodiments, the EPA and DHA esters constitute from at least about 40% to about 95% (wt/wt) of the total Omega-3 fatty acid esters in the composition. In certain embodiments, the EPA and DHA esters comprise about 40%, 45%, 50%, 55%, 60%, 65%, 70%, 75%, 80%, 85%, 90%, or 95% (wt/wt) of the total Omega-3 fatty acid esters of the composition.

It has been discovered that compositions comprising Omega-3 fatty acid esters having a ratio of more than 2.0:1.0 to not more than 3.4:1.0 of alkyl (5Z,8Z,11Z,14Z,17Z)-eicosa-5,8,11,14,17-pentenoate to alkyl (4Z,7Z,10Z,13Z,16Z,19Z)-docosa-4,7,10,13,16,19-hexaenoate (EPA:DHA) are effective for the reduction of TG concentrations in blood serum. In certain embodiments, the EPA and DHA esters comprise at least 40% of the total Omega-3 fatty acid esters of the composition. In certain embodiments, the EPA and DHA esters comprise about 40%, 45%, 50%, 55%, 60%, 65%, 70%, 75%, 80%, 85%, 90%, or 95% of the total Omega-3 fatty acid esters of the composition. It also has been discovered that compositions having Omega-3 fatty acid esters including more than about 2.0:1.0 to not more than 3.4:1.0 (EPA:DHA esters) can be formulated with one or more surface active agents to produce compositions that self-micellize in an aqueous medium. The micelles are generally uniformly spherical and stable, and provide for absorption of the Omega-3 fatty acid esters substantially free of any food effect. Based on the observation that the compositions described herein self-micellize in 0.1N HCl, it is believed that the compositions described herein will also self-micellize in the stomach or small intestine. In certain embodiments, such compositions provide beneficial drug delivery profiles for Omega-3 fatty acid esters.

In certain embodiments, the compositions described herein, comprising EPA and DHA esters, eliminate many of the side effects commonly associated with administration of Omega-3 fatty acid esters. Thus, the compositions described herein, comprising EPA and DHA esters, do not have a bad smell, and/or produce an unpleasant aftertaste, and/or cause burping in the patient. In another aspect, a composition is provided comprising at least one (5Z,8Z,11Z,14Z,17Z)-eicosa-5,8,11,14,17-pentenoic acid (EPA) ester; or at least one (4Z,7Z,10Z,13Z,16Z,19Z)-docosa-4,7,10,13,16,19-hexaenoic acid (DHA) ester; or a combination thereof, wherein the composition has a ratio of EPA ester to DHA ester of more than about 2.0:1.0 to not more than about 3.4:1.0, and at least one surface active agent; wherein said EPA ester, DHA ester, or a combination thereof, comprises at least 40% of the total amount of Omega-3 fatty acid esters in said composition. In certain embodiments, the Omega-3 fatty acid esters in said composition comprise Omega-3 fatty acid esters. In certain embodiments, the EPA and DHA esters constitute at least from about 40% to about 95% of the total Omega-3 fatty acid esters of the composition. Accordingly, in certain embodiments, the EPA and DHA esters comprise about 40%, 45%, 50%, 55%, 60%, 65%, 70%, 75%, 80%, 85%, 90% or 95% of the total Omega-3 fatty acid esters of the composition.

In certain embodiments, the ratio of EPA fatty acid ester to DHA ester is from more than 2.0:1.0 to not more than 3.4:1.0. In certain embodiments, the ratio of EPA ester to DHA ester is from about 2.0:1 to about 3.4:1.0. In other embodiments, the ratio of EPA ester to DHA ester is from about 2.0:1.0 to about 3.0:1.0. In other embodiments, the ratio of EPA ester to DHA ester is from about 2.0:1.0 to about 2.7:1.0. In other embodiments, the ratio of EPA ester to DHA ester is from about 2.0:1.0 to about 2.5:1.0. In other embodiments, the ratio of EPA ester to DHA ester is from about 2.0:1.0 to about 2.4:1.0. In other embodiments, the ratio of EPA ester to DHA ester is from about 2.1:1.0 to about 2.3:1.0. In other embodiments, the ratio of EPA ester to DHA ester is from about 2.1:1.0 to about 2.2:1.0. In other embodiments, the ratio of EPA ester to DHA ester is about 2.4:1.0.

In certain embodiments, said ratio of EPA ester to DHA ester in said composition is about 2.0:1.0. In certain embodiments, said ratio of EPA ester to DHA ester in said composition is about 2.1:1.0. In certain embodiments, said ratio of EPA ester to DHA ester in said composition is about 2.15:1.0.

In certain embodiments, said ratio of EPA ester to DHA ester in said composition is about 2.2:1.0. In certain embodiments, said ratio of EPA ester to DHA ester in said composition is about 2.3:1.0. In certain embodiments, said ratio of EPA ester to DHA ester in said composition is about 2.4:1.0. In certain embodiments, said ratio of EPA ester to DHA ester in said composition is about 2.5:1.0. In certain embodiments, said ratio of EPA ester to DHA ester in said composition is about 2.6:1.0. In certain embodiments, said ratio of EPA ester to DHA ester in said composition is about 2.7:1.0. In certain embodiments, said ratio of EPA ester to DHA ester in said composition is about 2.8:1.0. In certain embodiments, said ratio of EPA ester to DHA ester in said composition is about 2.9:1.0. In certain embodiments, said ratio of EPA ester to DHA ester in said composition is about 3.0:1.0. In certain embodiments, said ratio of EPA ester to DHA ester in said composition is about 3.1 1.0. In certain embodiments, said ratio of EPA ester to DHA ester in said composition is about 3.2:1.0. In certain embodiments, said ratio of EPA ester to DHA ester in said composition is about 3.3:1.0. In certain embodiments, said ratio of EPA ester to DHA ester in said composition is about 3.4:1.0.

In certain embodiments, the compositions described herein comprise an Omega-3 fatty acid ester selected from at least one of the following hexadecatrienoic acid ("HTA" or 16:3 (n-3), or all-Z-7,10,13-hexadecatrienoic acid), a-linolenic acid ("ALA" or 18:3 (n-3), or all-Z-9,12,15-octadecatrienoic acid), stearidonic acid ("SDA" or 18:4 (n-3) or all-Z-6,9,12,15-octadecatetraenoic acid), eicosatrienoic acid ("ETE" or 20:3 (n-3) or all-Z-11, 14, 17 eicosatrienoic acid), eicosatetraenoic acid ("ETA" or 20:4 (n-3), or all-Z-8,11,14,17-eicosatetraenoic acid), eicosapentaenoic acid ("EPA" or 20:5 (n-3) or all-Z-5,8,11,14,17-eicosapentaenoic acid), heneicosapentaenoic acid ("HPA" or 21:5 (n-3) or all-Z-6,9,12,15,18-heneicosapentaenoic acid), docosapentenoic acid ("DPA", or clupanodonic acid or 22:5 (n-3) or all-Z-7,10,13,16,19-docosapentenoic acid); docosahexaenoic acid ("DHA" or 22:6 (n-3) or all-Z-4,7,10,13,16,19-docosahexaenoic acid), tetracosapentenoic acid (24:5 (n-3) or all-Z-9,12,15,18,21-tetracosapentenoic acid), tetracosahexaenoic acid (nisinic acid or 24:6 (n-3) or all-Z-6,9,12,15,18,21-tetracosahexaenoic acid. In certain embodiments provided herein, the esters comprise an ester of (5Z,8Z,11Z,14Z,17Z)-eicosa-5,8,11,14,17-pentenoic acid (EPA), an ester of (4Z,7Z,10Z,13Z,16Z,19Z)-docosa-4,7,10,13,16,19-hexaenoic acid (DHA), or a combination thereof. In certain embodiments, the esters are ethyl esters. In certain embodiments, the esters are a single Omega-3 fatty acid ester. In certain embodiments, the esters are combinations of different Omega-3 fatty acid esters, such as those recited herein. In certain embodiments, other fatty acids, or dietary oils can also be present.

In certain embodiments, said Omega-3 fatty acid ester(s) comprise about 40% (wt/wt) of said composition. In certain embodiments, said Omega-3 fatty acid ester(s) comprise at about 45% (wt/wt) of said composition. In certain embodiments, said Omega-3 fatty acid ester(s) comprise about 50% (wt/wt) of said composition. In other embodiments, said Omega-3 fatty acid ester(s) comprise about 55% (wt/wt) of said composition. In other embodiments, said Omega-3 fatty acid ester(s) comprise about 60% (wt/wt) of said composition. In other embodiments, said Omega-3 fatty acid ester(s) comprise about 65% (wt/wt) of said composition. In other embodiments, said Omega-3 fatty acid ester(s) comprise about 70% (wt/wt) of said composition. In other embodiments, said Omega-3 fatty acid ester(s) comprise about 75% (wt/wt) of said composition. In other embodiments, the Omega-3 fatty acid ester(s) comprise about 80% (wt/wt) of said composition. In other embodiments, the Omega-3 fatty acid ester(s) comprise about 85% (wt/wt) of said composition. In other embodiments, the Omega-3 fatty acid ester(s) comprise about 90% (wt/wt) of said composition. In other embodiments, the Omega-3 fatty acid ester(s) comprise about 95% (wt/wt) of said composition.

In certain embodiments, the compositions comprise a pharmaceutical composition comprising a first Omega-3 fatty acid ester selected from the group consisting of an ester of hexadecatrienoic acid, α-linolenic acid, stearidonic acid, eicosatrienoic acid, eicosapentaenoic acid, heneicosapentaenoic acid, docosapentenoic acid, docosahexaenoic acid, tetracosapentenoic acid, tetracosahexaenoic acid, or combinations thereof; and a second Omega-3 fatty acid ester selected from the group consisting of an ester of hexadecatrienoic acid, α-linolenic acid, stearidonic acid, eicosatrienoic acid, eicosapentaenoic acid, heneicosapentaenoic acid, docosapentenoic acid, docosahexaenoic acid, tetracosapentenoic acid, tetracosahexaenoic acid, or combinations thereof and at least one surface active agent. The first and second Omega-3 fatty acid esters to be selected will be different. The ratio of the first to second Omega-3 fatty acid esters should be from more than 2:1 to not more than 3.4:1 (first Omega-3 fatty acid ester:second Omega-3 fatty acid ester). Typically, the ratio of the first to second Omega-3 fatty acid ester is about 2.4:1. The first and second Omega-3 fatty acid esters combined comprise from about 40% to about 85% (wt/wt) of the composition. In certain embodiments, the first and second Omega-3 fatty acid esters combined comprise at least about 40% (wt/wt) of the composition. In certain embodiments, the first and second Omega-3 fatty acid esters combined comprise at least about 45% (wt/wt) of the composition. In certain embodiments, the first and second Omega-3 fatty acid esters combined comprise at least about 50% (wt/wt) of the composition. In certain embodiments, the first and second Omega-3 fatty acid esters combined comprise at least about 55% (wt/wt) of the composition. In certain embodiments, first and second Omega-3 fatty acid esters combined comprise at least about 60% (wt/wt) of the composition. In certain embodiments, the first and second Omega-3 fatty acid esters combined comprise at least about 65% (wt/wt) of the composition. In certain embodiments, the first and second Omega-3 fatty acid esters combined comprise at least about 70% (wt/wt) of the composition. In certain embodiments, first and second Omega-3 fatty acid esters combined comprise at least about 75% (wt/wt) of the composition. In certain embodiments, first and second Omega-3 fatty acid esters combined comprise at least about 80% (wt/wt) of the composition. In certain embodiments, first and second Omega-3 fatty acid esters combined comprise at least about 85% (wt/wt) of the composition. In certain embodiments, these mixed Omega-3 fatty acid ester compositions are substantially free of active ingredients other than said Omega-3 fatty acid esters. These mixed Omega-3 fatty acid ester compositions can further comprise at least one terpene and/or at least one antioxidant. The terpene is typically substantially pure d-limonene and is present from about 0.1% to about 5% (wt/wt) of said composition. Optionally, the composition can also further comprise natural orange oil from about 0.1% to about 5% (wt/wt) of said composition. The at least one surface active agent can be any one or more of the surface active agents described herein, but is typically a polysorbate and/or a poloxamer, such as for example, polysorbate 80 and PLURONIC® F87. The surface active agent is present from about 15% to about 31% (wt/wt) of the composition. The antioxidant(s) suitable for use in these mixed Omega-3 fatty acid ester compositions, include, but are not limited to tocopherols and/or tocotrienols and can be present from about 0.01% to about 5% (wt/wt) of the composition. In certain such embodiments, the tocopherols and/or tocotrienols can be present at about 0.01%, 0.05%, 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5% or 5% by weight of the compositions. In certain such embodiments, the antioxidant is a tocopherol present at about 0.4% by weight of the composition.

In certain embodiments, compositions comprise an Omega-3 fatty acid ester, such as an ethyl ester, one or more surface active agents. In certain embodiments, said surface active agent is selected from the group consisting of nonionic surface active agents, cationic surface active agents, anionic surface active agents, zwitterionic surface active agents, or combinations thereof. In some embodiments, the compositions include one or more non-ionic surface active agents. Non-ionic surface active agents generally have a hydrophobic group and a reactive hydrogen atom, for example aliphatic alcohols, acids, amides and alkyl phenols, with alkylene oxides, especially ethylene oxide either alone or in combination with propylene oxide. Examples of nonionic surfactant compounds include, but are not limited to, polyoxyethylene glycol sorbitan alkyl esters, block copolymers of polyethylene glycol and polypropylene glycol, ethylene glycol fatty acid esters, poly(ethylene glycol) fatty acid esters, propylene glycol fatty acid esters, poly(propylene glycol) fatty acid esters, glycol fatty acid esters, trimethylolpropane fatty acid esters, pentaerythritol fatty acid esters, glucoside derivatives, glycerin alkyl ether fatty acid esters, trimethylolpropane oxyethylene alkyl ethers, fatty acid amides, alkylolamides, alkylamine oxides, lanolin and its derivatives, castor oil derivatives, hardened castor oil derivatives, sterols and its derivatives, polyoxyethylene alkyl ethers, polyoxyethylene alkyl allyl ethers, polyoxyethylene alkylamine, polyoxyethylene fatty acid amides, polyoxyethylene alkylolamides, polyoxyethylene diethanolamine fatty acid esters, polyoxyethylene trimethylolpropane fatty acid esters, polyoxyethylene alkyl ether fatty acid esters, polyoxyethylene polyoxypropylene glycols, polyoxyethylene polyoxypropylene alkyl ethers, polyoxyethylene polyoxypropylene polyhydric alcohol ethers, glycerin fatty acid esters, polyglycerin fatty acid esters, polyoxyethylene glycerin fatty acid esters, sorbitan fatty acid esters, polyoxyethylene sorbitan fatty acid esters, sucrose fatty acid esters, or combinations thereof.

In certain embodiments, the surface active agents comprise polyoxyethylene glycol sorbitan alkyl esters, block copolymers of polyethylene glycol and polypropylene glycol, or combinations thereof.

Examples of polyoxyethylene glycol sorbitan alkyl esters are typically the polysorbates. Polysorbates are a class of oily liquids derived from PEG-ylated sorbitan (a derivative of sorbitol) esterified with fatty acids. Common brand names for polysorbates include TWEEN®. TWEEN®-20, TWEEN®-60 and TWEEN®-80, for example, are available from AkzoNobel (Strawinskylaan 2555 1077 ZZ, Amsterdam, the Netherlands). Exemplary polysorbates include polysorbate 20 (polyoxyethylene (20) sorbitan monolaurate), polysorbate 40 (polyoxyethylene (20) sorbitan monopalmitate), polysorbate 60 (polyoxyethylene (20) sorbitan monostearate), and polysorbate 80 (polyoxyethylene (20) sorbitan monooleate).

Examples of block copolymers of polyethylene glycol and polypropylene glycol include the poloxamers. Poloxamers are nonionic triblock copolymers composed of a central hydrophobic chain of polyoxypropylene (poly(propylene oxide)) flanked by two hydrophilic chains of polyoxyethylene (poly(ethylene oxide)). Certain poloxamers, such as those listed herein, are also known by the trade names PLURONIC® available from suppliers such as BASF AG (Ludwigshafen, Germany). Because the lengths of the polymer blocks can be customized, many different poloxamers exist that have slightly different properties. Further exemplary PLURONIC® poloxamers include, but are not limited to PLURONIC® 10R5, PLURONIC® 17R2, PLURONIC® 17R4, PLURONIC® 25R2, PLURONIC® 25R4, PLURONIC® 31R1, PLURONIC® F 108 Cast Solid Surfacta, PLURONIC® F 108 NF, PLURONIC® F 108 Pastille, PLURONIC® F 108 Prill, PLURONIC® F 108NF Prill Poloxamer 338, PLURONIC® F 127, PLURONIC® F 127 Prill, PLURONIC® F 127 NF, PLURONIC® F 127 NF 500 BHT Prill, PLURONIC® F 127 NF Prill Poloxamer 407, PLURONIC® F 38, PLURONIC® F 38 Pastille, PLURONIC® F 68, PLURONIC® F 68 Pastille, PLURONIC® F 68 LF Pastille, PLURONIC® F 68 NF, PLURONIC® F 68 NF Prill Poloxamer 188, PLURONIC® F 68 Prill, PLURONIC® F 68 Prill, PLURONIC® F 77, PLURONIC® F 77 Micropastille, PLURONIC® F 87, PLURONIC® F 87 NF, PLURONIC® F 87 NF Prill Poloxamer 237, PLURONIC® F 87 Prill, PLURONIC® F 88, PLURONIC® F 88 Pastille, PLURONIC® F 88 Prill, PLURONIC® F 98, PLURONIC® F 88 Prill, PLURONIC® F 98, PLURONIC® F 98 Prill, PLURONIC® L 10, PLURONIC® L 101, PLURONIC® L 121, PLURONIC® L 31, PLURONIC® L 35, PLURONIC® L 43, PLURONIC® L 44, PLURONIC® L 61, PLURONIC® L 62, PLURONIC® L 62 LF, PLURONIC® L 62D, PLURONIC® L 64, PLURONIC® L 81, PLURONIC® L 92, PLURONIC® L 44 NF INH surfactant Poloxamer 124, PLURONIC® N 3, PLURONIC® P 103, PLURONIC® P 104, PLURONIC® P 105, PLURONIC® P 123 Surfactant, PLURONIC® P 65, PLURONIC® P 84, PLURONIC® P 85, or combinations thereof.

In certain embodiments, the composition comprises from about 15% (wt/wt) to about 31% (wt/wt) polysorbate. In certain embodiments, said polysorbate is polysorbate 80. In other embodiments, the composition comprises from about 0.5% (wt/wt) to about 5% (wt/wt) poloxamer. In certain embodiments, the polysorbate is polysorbate 20, polysorbate 60, polysorbate 80 or a combination thereof, and the poloxamer is PLURONIC® F 87, PLURONIC® L61, PLURONIC® F 127, or a combination thereof. In some embodiments, the composition comprises Omega-3 fatty acid esters, such as ethyl esters, in an amount from about 50% (wt/wt) to about 80% (wt/wt); and polysorbate from about 15% (wt/wt) to about 99% (wt/wt); and poloxamer from about 0.05% (wt/wt) to about 50% (wt/wt). In certain embodiments, the at least one surface active agent is a combination of a polysorbate, such as for example polysorbate 80, from about 15% (wt/wt) to about 31% (wt/wt) of said composition, and a poloxamer, such as for example PLURONIC® F87, from about 0.5% (wt/wt) to about 5% (wt/wt) of said composition.

In certain embodiments, said polysorbate comprises about 15% (wt/wt) to about 70% (wt/wt) of said composition. In certain embodiments, said polysorbate comprises about 15% (wt/wt) to about 50% (wt/wt) of said composition. In certain embodiments, said polysorbate comprises about 15% (wt/wt) to about 31% (wt/wt) of said composition. In certain embodiments, said polysorbate comprises about 15% (wt/wt) to about 25% (wt/wt) of said composition. In certain embodiments, said polysorbate comprises about 15% (wt/wt) to about 20% (wt/wt) of said composition. In certain embodiments, said polysorbate comprises about 20% (wt/wt) to about 31% (wt/wt) of said composition.

In certain embodiments, the poloxamer comprises from about 0.5% (wt/wt) to about 5% (wt/wt) of said composition. In certain embodiments, the poloxamer comprises from about 0.5% (wt/wt) to about 4% (wt/wt) of said composition. In certain embodiments, the poloxamer comprises from about 0.5% (wt/wt) to about 3% (wt/wt) of said composition. In certain embodiments, the poloxamer comprises from about 0.5% (wt/wt) to about 2% (wt/wt) of said composition. In certain embodiments, the poloxamer comprises from about 0.5% (wt/wt) to about 1% (wt/wt) of said composition.

In some embodiments, the compositions include one or more anionic surface active agents. Exemplary "anionic surface active agents" include, but are not limited to, N-acyl-L-glutamic acid diethanolamine, N-acyl-L-glutamic acid triethanolamine, sodium N-acyl-L-glutamate, sodium alkanesulfonate, ammonium alkyl (C12, C14, C16) sulfate, alkyl (C11, C13, C15) sulfuric acid triethanolamine, alkyl (C11, C13, C15) sulfuric acid triethanolamine, alkyl (C12 to C14) sulfuric acid triethanolamine, liquid alkylsulfuric acid triethanolamine, sodium alkyl (C12, C13) sulfate, liquid sodium alkylsulfate, sodium isoethionate, sodium lacto-isostearate, disodium undecylenoylamido ethyl sulfosuccinate, triethanolamine sulfooleate, sodium sulfooleate, disodium oleamide sulfosuccinate, potassium oleate, sodium oleate, morpholine oleate, oleoyl sarcosine, oleoyl methyltaurine sodium salt, potassium-containing soap base, liquid base for potassium soap, potassium soap, carboxylated polyoxyethylene tridodecyl ether, sodium salt (3 ethyle oxide "E.O.") of carboxylated polyoxyethylene tridodecyl ether, triethanolamine N-hydrogenated tallow fatty-acyl-L-glutamate, sodium N-hydrogenated tallow fatty-acyl-L-glutamate, sodium hydrogenated coconut fatty acid glyceryl sulfate, sodium diundecylenoylamido ethyl sulfosuccinate, sodium stearyl sulfate, potassium stearate, triethanolamine stearate, sodium stearate, sodium N-stearoyl-L-glutamate, disodium stearoyl-L-glutamate, stearoyl methyltaurine sodium salt, sodium dioctyl sulfosuccinate, liquid sodium dioctyl sulfosuccinate, liquid disodium polyoxyethylene monooleylamido sulfosuccinate (2 E.O.), disodium polyoxyethylene lauroyl ethanolamide sulfosuccinate (5 E.O.), disodium lauryl sulfosuccinate, diethanolamide cetyl sulfate, sodium cetyl sulfate, soap base, sodium cetostearyl sulfate, triethanolamine tridecyl sulfate, potassium palmitate, sodium palmitate, palmitoyl methyltaurine sodium salt, liquid castor oil fatty acid sodium salt (30%), ammonium polyoxyethylene alkyl ether sulfate (3 E.O.), liquid diethanolamine polyoxyethylene alkyl (C12, C13) ether sulfate, liquid triethanolamine polyoxyethylene alkyl ether sulfate (3 E.O.), triethanolamine polyoxyethylene alkyl (C11, C13, C15) ether sulfate (1 E.O.), triethanolamine polyoxyethylene alkyl (C12, C13) ether sulfate (3 E.O.), liquid sodium polyoxyethylene alkyl ether sulfate (3 E.O.), sodium polyoxyethylene alkyl (C11, C13, C15) ether sulfate (1 E.O.), sodium polyoxyethylene alkyl (C11 to C15) ether sulfate (3 E.O.), sodium polyoxyethylene alkyl (C12, C13) ether sulfate (3 E.O.), sodium polyoxyethylene alkyl (C12 to C14) ether sulfate (3 E.O.), sodium polyoxyethylene alkyl (C12 to C15) ether sulfate (3 E.O.), disodium polyoxyethylene alkyl (C12 to C14) sulfosuccinate (7 E.O.), sodium polyoxyethylene undecyl ether sulfate, liquid sodium polyoxyethylene octyl phenyl ether sulfate, ammonium polyoxyethylene oleyl ether sulfate, disodium polyoxyethylene lauryl sulfosuccinate, sodium polyoxyethylene nonyl phenyl ether sulfate, sodium polyoxyethylene pentadecyl ether sulfate, triethanolamine polyoxyethylene myristyl ether sulfate, sodium polyoxyethylene myristyl ether sulfate, sodium polyoxyethylene myristyl ether sulfate (3 E.O.), liquid sodium polyoxyethylene lauryl ether acetate (16 E.O.), ammonium polyoxyethylene lauryl ether sulfate (2 E.O.), triethanolamine polyoxyethylene lauryl ether sulfate, sodium polyoxyethylene lauryl ether sulfate, diethanolamine myristyl sulfate, sodium myristyl sulfate, potassium myristyl sulfate, sodium N-myristoyl-L-glutamate, sodium myristoylmethylaminoacetate, liquid myristoyl methyl-alanine sodium salt, myristoyl methyltaurine sodium salt, medicinal soaps, triethanolamine/magnesium coco alkyl sulfate, triethanolamine N-coconut oil fatty-acyl-L-glutamate, sodium N-coconut oil fatty-acyl-L-glutamate, sodium coconut oil fatty acid ethyl ester sulfonate, coconut oil fatty acid potassium salt, liquid coconut oil fatty acid potassium salt, sodium N-coconut oil fatty/hydrogenated fatty-acyl-L-glutamate, coconut oil fatty acid sarcosine, coconut oil fatty acid sarcosine triethanolamine salt, coconut oil fatty acid sarcosine sodium salt, coconut oil fatty acid triethanolamine salt, liquid triethanolamine salt of coconut oil fatty acid, coconut oil fatty acid sodium salt, coconut oil fatty acid methyl alanine sodium salt, liquid coconut oil fatty acid methyl alanine sodium salt, coconut oil fatty acid methyltaurine potassium salt, coconut oil fatty acid methyltaurine sodium salt, sodium laurylamino dipropionate, liquid sodium laurylamino dipropionate (30%), sodium lauryl sulfoacetate; sodium lauryl benzenesulfonate, lauryl sulfate, ammonium lauryl sulate, potassium lauryl sulfate, diethanolamine lauryl sulfate, triethanolamine lauryl sulfate, sodium lauryl sulfate, magnesium lauryl sulfate, monoethanolainine lauryl sulfate, potassium laurate, lauric acid triethanolamine, liquid lauric acid triethanolamine, sodium laurate, lauric acid/myristic acid triethanolamine, lauroyl-L-glutamic acid triethanolamine, sodium N-lauroyl-L-glutamate, lauroyl sarcosine, lauroyl sarcosine potassium, liquid lauroyl sarcosine triethanolamine salt, lauroyl sarcosine sodium, liquid lauroyl methyl-.beta.-alanine sodium salt, lauroyl methyltaurine sodium salt, liquid lauroyl methyltaurine sodium salt, or combinations thereof.

In certain embodiments, said anionic surfactant(s) comprise about 0.05% (wt/wt) to about 25% (wt/wt) of said composition. In certain embodiments, said anionic surfactant(s) comprise about 0.05% (wt/wt) to about 15% (wt/wt) of said composition. In certain embodiments, said anionic surfactant(s) comprise about 0.05% (wt/wt) to about 5% (wt/wt) of said composition. In certain embodiments, said anionic surfactant(s) comprise about 0.5% (wt/wt) to about 3% (wt/wt) of said composition. In certain embodiments, said anionic surfactant(s) comprise about 0.7% (wt/wt) of said composition. In certain embodiments, said anionic surfactant(s) comprise sodium lauryl sulfate.

In certain embodiments, compositions comprise an Omega-3 fatty acid ester, such as an ethyl ester, and further comprise one or more surface active agents. In certain embodiments, said surface active agent is selected from the group consisting of a polysorbate or a combination of polysorbates, and an anionic surfactant or a combination of anionic surfactants, or a combination of said polysorbates and said anionic surfactants. In other embodiments, the composition comprises from about 15% (wt/wt) to about 31% (wt/wt) polysorbate. In certain embodiments, said polysorbate is polysorbate 80. In other embodiments, the composition comprises from about 0.5% (wt/wt) to about 5% (wt/wt) anionic surfactant(s). In certain embodiments, the polysorbate is polysorbate 80, polysorbate 20, or a combination thereof, and the anionic surfactant is sodium lauryl sulfate. In some embodiments, the composition comprises Omega-3 fatty acid esters, such as ethyl esters, in an amount from about 40% (wt/wt) to about 85% (wt/wt); and polysorbate from about 15% (wt/wt) to about 99% (wt/wt); and anionic surfactant(s) from about 0.05% (wt/wt) to about 50% (wt/wt). In some embodiments, the composition comprises Omega-3 fatty acid esters, such as ethyl esters, in an amount from about 50% (wt/wt) to about 80% (wt/wt) (90); and polysorbate from about 15% (wt/wt) to about 99% (wt/wt); and anionic surfactant(s) such as, for example, sodium lauryl sulfate from about 0.05% (wt/wt) to about 2% (wt/wt). In some embodiments, the composition comprises about 0.7% (wt/wt) sodium lauryl sulfate.

In certain embodiments, said poloxamer comprises about 0.05% (wt/wt) to about 25% (wt/wt) of said composition. In certain embodiments, said poloxamer comprises about 0.05% (wt/wt) to about 15% (wt/wt) of said composition. In certain embodiments, said poloxamer comprises about 0.05% (wt/wt) to about 5% (wt/wt) of said composition. In certain embodiments, said poloxamer comprises about 0.5% (wt/wt) to about 3% (wt/wt) of said composition.

In some embodiments, the compositions include additional surface active agents such as the zwitterionic and cationic surface active agents. Examples of such surface active agents include, but are not limited to the bile acids (e.g., cholic acid, chenodeoxycholic acid, glycocholic acid, glycodeoxycholic acid, taurocholic acid, taurochenodeoxycholic acid, taurolithocholic acid, deoxycholic acid, lithocholic acid, and ursodeoxycholic acid and salts thereof, e.g., sodium, potassium, lithium), natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methyl cellulose), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyllaurate, sodium lauryl sulfate, cetrimonium bromide, cetylpyridinium chloride, benzalkonium chloride, docusate sodium or combinations thereof.

Compositions suitable for self-micellization as described herein generally have an HLB from about 12 to about 18. In certain embodiments, said compositions have an HLB from about 12.0 to about 14.0. In certain embodiments, said compositions have an HLB from about 13.0 to about 14.0. In certain embodiments, said compositions have an HLB from about 13.5 to about 13.8. The total HLB of all the surface active agents or surfactants used in the composition is generally from about 12 to about 18. In some embodiments, the total HLB of all surface active agents used in the composition is generally from about 12 to about 15. In some embodiments, the total HLB of all surface active agents or surfactants used in the composition is generally from about 13 to about 15.

In certain embodiments, the at least one surface active agent or surfactant has a HLB of at least 8.0. In some embodiments, said surface active agent(s) or surfactant(s) have a combined HLB in the range of from about 13 to about 15. As the HLB value of the surface active agent(s) or surfactant(s) increases, the amount of surface active agent or surfactant needs to be decreased, such that at an HLB of 17, only about 25% (wt/wt) to about 42% (wt/wt) of surface active agent(s) or surfactant(s) may be required.

In certain embodiments, the composition further comprises a terpene. In certain embodiments, the terpene is d-limonene. In one embodiment, the terpene is a cyclic terpene. In one embodiment, the terpene is d-limonene ((+)-limonene), which is the (R)-enantiomer. In one embodiment, the terpene is L-limonene, which is the (S)-enantiomer. In one embodiment, the terpene is racemic limonene, known as dipentene. In another embodiment, the terpene is a terpenoid. In another embodiment, the terpene or terpenes are derived from a natural oil (e.g., a citrus oil such as orange oil). Other terpenes are contemplated, such as monoterpenes (e.g., terpinenes, terpinolenes, phellandrenes, or menthol), having structures that are similar to d-limonene. In certain embodiments, the compositions further comprise substantially pure d-limonene from about 0.1% to about 5% by weight of the composition. In certain other embodiments, the compositions further comprise natural orange oil from about 0.1% to about 5% by weight of the composition. Compositions comprising d-limonene or orange oil can aid in the elimination and/or minimization of side effects from the oral administration of Omega-3 fatty acid esters. Such side effects include regurgitation, frequency of belching, gastroesophageal reflux disease (GERD), bloating, increased intestinal gas, fish taste, fishy breath, fish smell, nausea, diarrhea, or combinations thereof.

In other embodiments, the composition further comprises an antioxidant. In certain embodiments, the antioxidant is selected from the consisting of at least one tocopherol, at least one tocotirenol, or combinations thereof. In other embodiments, the compositions described herein may include one or more tocopherol(s). In embodiments further comprising the at least one or more antioxidant(s), the antioxidant(s) can be present from about 0.01% to about 5% by weight of the compositions. In such embodiments, the antioxidant(s) can be present at about 0.01%, 0.05%, 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5% or 5% by weight of the compositions. In certain embodiments, the antioxidant(s) can be present at about 0.4% by weight of the compositions.

In an at least one additional embodiment, compositions comprising micelles are provided, wherein the micelles are formed by the addition of an aqueous medium to a composition of any one of the embodiments provided herein prior to administration of said composition to a subject in need of treatment. Alternatively, micelles can also be formed when the compositions are added to an aqueous medium. In certain embodiments, the micelles have a diameter of up to about 10 μm. In other embodiments, substantially all of the micelles have an average diameter of from about 1 μm to about 10 μm. In certain embodiments, the micelles have an average diameter of about 1, 2, 3, 4, 5, 6, 7, 8, 9 or 10 μm. In certain embodiments, said micelles are stable at room temperature. In certain embodiments, the composition forms micelles in an aqueous medium having an acidic pH. In certain other embodiments, the compositions form micelles in 0.1N HCl.

In another embodiment, a composition is provided, wherein said composition comprises at least one (5Z,8Z,11Z, 14Z,17Z)-eicosa-5,8,11,14,17-pentenoic acid (EPA) ester and at least one (4Z,7Z,10Z,13Z,16Z,19Z)-docosa-4,7,10, 13,16,19-hexaenoic acid (DHA) ester, and wherein said composition has a ratio of EPA ester to DHA ester of more than 2.0:1.0 to not more than about 3.4:1.0, provided that the concentration of said EPA ester, DHA ester, or a combination thereof comprises from about 40% to about 85% by weight of the total amount of Omega 3 esters in said composition. In certain embodiments, the ratio of EPA ester to DHA ester is from about 2.0:1.0 to about 2.5:1.0. In other embodiments, the ratio of EPA ester to DHA ester is from about 2.1:1.0 to about 2.4:1.0. In other embodiments, the ratio of EPA ester to DHA ester is from about 2.1:1.0 to about 2.3:1.0. In other embodiments, the ratio of EPA ester to DHA ester is from about 2.1:1.0 to about 2.2:1.0. In certain embodiments, said ratio of EPA ester to DHA ester in said composition is 2.4:1.0. In other embodiments, the ratio of EPA ester to DHA ester is from about 2.0:1.0 to about 3.3:1.0. In other embodiments, the ratio of EPA ester to DHA ester is from about 2.2:1.0 to about 3.2:1.0. In other embodiments, the ratio of EPA ester to DHA ester is from about 2.4:1.0 to about 3.1:1.0. In other embodiments, the ratio of EPA ester to DHA ester is from about 2.5:1.0 to about 3.0:1.0. In other embodiments, the ratio of EPA ester to DHA ester is from about 2.6:1.0 to about 2.9:1.0. In other embodiments, the ratio of EPA ester to DHA ester is from about 2.7:1.0 to about 2.8:1.0. In certain embodiments, said ratio of EPA ester to DHA ester in said composition is more than 2.0:1.0.

In certain embodiments, the Omega-3 fatty acid esters used herein are substantially pure. In certain embodiments, the Omega-3 fatty acid esters are from about 80% to about 99% pure. In certain embodiments, the Omega-3 fatty acid esters are at least 80%, 85%, 90%, 92%, 94%, 96%, 98% or 99% pure.

Methods for Treating Cardiovascular Conditions or Disorders

Methods are provided of treating one or more cardiovascular condition or disorder in a subject in need of treatment, which method comprises administering to said subject a therapeutically effective amount of a composition of any one of the embodiments provided herein, or a micelle of any one of the embodiments provided herein.

Accordingly, in certain embodiments, the cardiovascular condition or disorder is of the heart and vasculature, including, for example, hypertension, hyperlipidemia, hypertriglyceridemia, atherosclerosis, transient ischemic attack, systolic dysfunction, diastolic dysfunction, aneurysm, aortic dissection, myocardial ischemia, acute myocardial infarction (AMI), acute ST-segment elevation myocardial infarction (STEMI), acute non-ST-segment elevation myocardial infarction (NSTEMI), angina pectoris, unstable angina (UA), and stable angina (SA), myocardial infarction, congestive heart failure, dilated congestive cardiomyopathy, hypertrophic cardiomyopathy, restrictive cardiomyopathy, corpulmonale, arrhythmia, valvular heart disease, endocarditis, pulmonary embolism, venous thrombosis, peripheral vascular disease, and peripheral artery disease.

In particular embodiments, the cardiovascular condition or disorder is hypertension, hyperlipidemia, or a combination thereof. In other embodiments, the cardiovascular condition or disorder is hypertriglyceridemia.

In another embodiment, a method is provided for treating moderate to severe hypertriglyceridemia in a subject in need thereof, wherein the method comprises providing a subject having a fasting baseline TG level of about 200 mg/dL to about 500 mg/dL and administering to the subject a composition as described herein. In one embodiment, the composition can be administered in a daily amount of from about 0.5 g to about 1 g, from about 1 g to about 2 g, from about 2 g to about 4 g, from about 4 g to about 6 g, or from about 6 g to about 10 g.

In certain embodiments, the amount of total fasting TG in the subject's blood serum is reduced by at least 20% within thirty days of administration of said composition or said micelles in a subject having at least 150 mg/dL fasting blood serum TG at the start of the dosing regimen. In other embodiments, the total concentration of low-density lipoprotein (LDL) in said subject's blood serum does not substantially increase within thirty days of administration of said composition or said micelles. In certain embodiments, the therapeutically effective amount of said composition or said micelles comprises at least 0.5 g/day of the Omega-3 fatty acid esters. In other embodiments, said subject's blood serum has a concentration of at least 20 nmol/mL of combined EPA, DHA or combinations thereof within four hours after administration of said composition or said micelles.

In further embodiments, a method is provided of administering to a subject a composition comprising at least one Omega-3 fatty acid ester wherein the ratio of high-density lipoprotein is increased relative to LDL in the blood serum of the subject. In certain embodiments, the administration is an oral administration. In certain embodiments, the subject is a human.

Some embodiments provide for a method of administering to a subject a composition comprising at least one Omega-3 fatty acid ester and at least one surface active agent, wherein said at least one Omega-3 fatty acid ester self-micellizes when in contact with an aqueous medium, and said at least one Omega-3 fatty acid ester when orally administered is absorbed by said subject at a rate that is substantially independent of a food effect. In certain embodiments, the reduction of the food effect may yield a reduction in F of at least 30%, at least 40%, at least 50%, or at least 75%.

A method is provided of administering to a subject a composition comprising at least one Omega-3 fatty acid ester and at least one surface active agent, wherein said at least one Omega-3 fatty acid ester self-micellizes when in contact with an aqueous medium, and said at least one Omega-3 fatty acid ester when orally administered is absorbed by said subject at a rate that is substantially independent of a food effect. In certain embodiments, said composition is a composition of any one of the embodiments provided herein. In other embodiments, at least 0.5 g/day of the Omega-3 fatty acid ester is administered to said subject.

In another embodiment, the composition as described herein is administered, for example over a period of about 1 to about 200 weeks, about 1 to about 100 weeks, about 1 to about 80 weeks, about 1 to about 50 weeks, about 1 to about 40 weeks, about 1 to about 20 weeks, about 1 to about 15 weeks, about 1 to about 12 weeks, about 1 to about 10 weeks, about 1 to about 5 weeks, about 1 to about 2 weeks or about 1 week. In another embodiment, the composition as described herein is administered for an unlimited period of time to a subject in need of chronic treatment.

In other embodiments, said subject's blood serum has a concentration of at least 20 nmol/mL of said at least one Omega-3 fatty acid ester within four hours after administration of said composition. In other embodiments, said subject's blood serum has a concentration of at least 50 nmol/mL of said at least one Omega-3 fatty acid ester within four hours after administration of said composition. In other embodiments, said subject's blood serum has a concentration of at least 100 nmol/mL of said at least one Omega-3 fatty acid ester within four hours after administration of said composition. In other embodiments, the concentration of said at least one Omega-3 fatty acid ester in said subject's blood serum can be increased upon the administration of increasing doses of said composition.

In certain embodiments, a method is provided of minimizing and/or eliminating side effects from the oral administration of Omega-3 fatty acid esters in the presence of a surface active agent to a subject in need of treatment comprising administering a composition of any one of the embodiments provided herein or the micelles of any one of the embodiments provided herein. In certain embodiments, the method of minimizing side effects eliminates the onset of side effects. In some embodiments, non-limiting examples of the side effects include regurgitation, frequency of belching, gastroesophageal reflux disease (GERD), bloating, increased intestinal gas, fish taste, fishy breath, fish smell, nausea, diarrhea, or combinations thereof.

In certain embodiments, a method is provided of minimizing and/or eliminating side effects from the oral administration of Omega-3 fatty acid esters in the presence of at least one terpene or natural orange oil to a subject in need of treatment comprising administering a composition of any one of the embodiments provided herein or the micelles of any one of the embodiments provided herein. In certain embodiments, the at least one terpene is typically, but not necessarily d-limonene that is at least 95% pure. In certain embodiments, the method of minimizing side effects eliminates the onset of side effects. In some embodiments, non-limiting examples of the side effects include regurgitation, frequency of belching, gastroesophageal reflux disease (GERD), bloating, increased intestinal gas, fish taste, fishy breath, fish smell, nausea, diarrhea, or combinations thereof.

Some embodiments provide for a method of reducing a food effect in a subject in need of treatment, which method comprises administering to a human subject a therapeutically effective amount of any one of the compositions described herein. In certain embodiments, the food effect is substantially eliminated.

Methods are also provided for improving patient compliance during the oral administration of Omega-3 fatty acid esters to a subject in need of treatment comprising administering a composition as described herein.

The compositions described herein can be administered to a human subject in need of such administration with a non-Omega-3 fatty acid ester lipid-lowering or cholesterol lowering agent selected from the group consisting of cholesterol absorption inhibitors, bile acid sequestrants/resins, statins, niacin and derivatives, MTP inhibitors, fibrates and CETP inhibitors. These lipid-lowering or cholesterol lowering agents can be categorized by their mechanism of action. For example, cholesterol absorption inhibitors inhibit absorption of dietary cholesterol and inhibit reabsorption of biliary cholesterol. Examples of cholesterol absorption inhibitors include, but are not limited to, phytosterols, ezetimibe, and (3R,4S)-1,4-bis(4-methoxyphenyl)-3-(3-phenylpropyl)-2-azetidinone (SCH 48461). Bile acid sequestrants/resins are polymeric compounds and function as ion exchange resins. Bile acid sequestrants exchange anions such as chloride ions for bile acids. By doing so, they bind bile acids and sequester them from enterohepatic circulation. Since bile acid sequesterants are large polymeric structures, they are not well-absorbed from the gut into the bloodstream. Thus, bile acid sequestrants, along with any bile acids bound to the drug, are excreted via the feces after passage through the gastrointestinal tract. Examples of bile acid sequestrants/resins include, but are not limited to cholestyramine, colesevelam, and colestipol. Statins are a class of compounds that inhibit the enzyme HMG-CoA reductase. Examples of statins include, but are not limited to rosuvastatin, lovastatin, fluvastatin, simvastatin, pravastatin, and atorvastatin. It is believed that niacin and its derivatives function by stimulating the G-protein coupled receptor GPR109A, which causes the inhibition of fat breakdown in adipose tissue. Examples of niacin and its derivatives include, but are not limited to, niceritrol, niacin, nicofuranose, aluminium nicotinate, nicotinyl alcohol, and acipimox. MTP (Microsomal Triglyceride Transfer Protein) is a lipid transfer protein that is required for the assembly and secretion of very low density lipoproteins by the liver and chylomicrons by the intestine. Accordingly, inhibitors of MTP decrease levels of plasma LDL-C. Examples of MTP inhibitors include, but are not limited to, lomitapide for human use and dirlotapide and mitrapatide for veterinary use in dogs. Rodent and human studies suggest that fibrates exert their hypolipidemic effects via several mechanisms. Examples of fibrates include, but are not limited to bezafibrate, ciprofibrate, clofibrate, gemfibrozil, and fenofibrate. CETP (Cholesterylester Transfer Protein) inhibitors improve blood plasma lipid profiles by increasing HDL ("good" cholesterol containing particle) and decreasing LDL ("bad" cholesterol containing particle). Examples of CETP inhibitors include, but are not limited to anacetrapib and evacetrapib.

In addition to the aforementioned disease states, several other conditions or disorders can also benefit from treatment with the compositions described herein, such as for example; metabolic syndrome; macular degeneration (AREDS2 Research Group et. al. The Age-Related Eye Disease 2 (AREDS2): study design and baseline characteristics (AREDS2 report number 1), Opthalmology. 2012 November 119(11):2282-9. doi 10.1016/j.optha 2012.05.027. Epub 2012 Jul. 26; SanGiovanni J P et. al., ω-3 long-chain polyunsaturated fatty acid intake and 12-y incidence of neovascular age-related macular degeneration and central geographic atrophy: AREDS report 30, a prospective cohort study from the Age-Related Eye Disease Study. Am. J. Clin. Nutr. 2009; 90:1601-70.); cognitive impairment resulting from surgery or traumatic brain injury, such as for example resulting from a concussion (Lewis M. et. al. Therapeutic use of omega-3 fatty acids in severe head trauma. Am J Emerg Med. 2013 January; 31(1):273.e5-8. doi: 10.1016/j.ajem.2012.05.014. Epub 2012 Aug. 3; Mills J D. et. al. Dietary supplementation with the omega-3 fatty acid docosahexaenoic acid in traumatic brain injury. Neurosurgery. 2011 February; 68(2):474-81; discussion 481. doi: 10.1227/NEU.0b013e3181ff692b.); major depression, suicide, post-partum depression (Logan A C. Omega-3 fatty acids and major depression: a primer for the mental health professional. Lipids Health Dis. 2004 Nov. 9; 3:25; Lewis M D et al. Suicide deaths of active-duty US military and omega-3 fatty-acid status: a case-control comparison. J Clin Psychiatry, 2011 December; 72(12):1585-90. doi: 10.4088/JCP.11m06879. Epub 2011 Aug. 23; Makrides M. et. al. Docosahexaenoic acid and post-partum depression—is there a link? Asia Pac J Clin Nutr. 2003; 12 Suppl: 537.); inflammation (Kelley D S et. al. DHA supplementation decreases serum C-reactive protein and other markers of inflammation in hypertriglyceridemic men. J Nutr. 2009 March; 139(3):495-501. doi: 10.3945/jn.108.100354. Epub 2009 Jan. 21.); primary sclerosing cholangitis (Martin C R. et. al. The safety and efficacy of oral docosahexaenoic acid supplementation for the treatment of primary sclerosing cholangitis—a pilot study. Aliment Pharmacol Ther. 2012 January; 35(2):255-65. doi: 10.1111/j.1365-2036.2011.04926.x. Epub 2011 Nov. 30.), borderline personality disorder in women (Zanarini M C et al. Omega-3 Fatty acid treatment of women with borderline personality disorder: a double-blind, placebo-controlled pilot study. Am J Psychiatry. 2003 January; 160(1):167-9.), breast cancer (Bougnoux P. et al. Improving outcome of chemotherapy of metastatic breast cancer by docosahexaenoic acid: a phase II trial. Br J Cancer, 2009 Dec. 15; 101(12):1978-85. doi: 10.1038/sj.bjc.6605441. Epub 2009 Nov. 17.), non-alcoholic fatty acid liver disease (Parker H M. et. al. Omega-3 supplementation and non-alcoholic fatty liver disease: a systematic review and meta-analysis. J Hepatol. 2012 April; 56(4):944-51. doi: 10.1016/j.jhep.2011.08.018. Epub 2011 Oct. 21;

Nobili V. Docosahexaenoic acid for the treatment of fatty liver: Randomised controlled trial in children. Nutr Metab Cardiovasc Dis. 2012 Dec. 7. pii: S0939-4753(12)00256-6. doi: 10.1016/j.numecd.2012.10.010. [Epub ahead of print]; Christopher M.D. et. al. Menhaden oil decreases high-fat diet-induced markers of hepatic damage, steatosis, inflammation, and fibrosis in obese Ldlr−/− mice. J Nutr. 2012 August; 142(8):1495-503. doi: 10.3945/jn.112.158865. Epub 2012 Jun. 27.), and improvement in cognition and behavior in children (Richardson A J. et. al. Docosahexaenoic acid for reading, cognition and behavior in children aged 7-9 years: a randomized, controlled trial (the DOLAB Study). PLoS One. 2012; 7(9):e43909. doi: 10.1371/journal.pone.0043909. Epub 2012 Sep. 6.). These conditions or disorders can be treated by administering the compositions described herein to a subject, typically a human, in need of such administration.

Kits

Packaged pharmaceutical kits are included herein. The kits comprise compositions described herein as unit dosage forms in a container and instructions for using the dosage form to treat a subject having a disease or disorder responsive to treatment by administration of the dosage forms comprising the compositions described herein.

The packaged pharmaceutical kits provide prescribing information, over the counter medical use information, and/or nutritional information for the dosage form including, for example and without limitation, to a subject or health care provider, or as a label in a packaged pharmaceutical kit. Information included in the kit may include, for example and without limitation, efficacy, dosage and administration, contraindication and adverse reaction information pertaining to the Omega-3 fatty acid dosage form. The dosage and administration information, for example, can include dosing frequency as well as administration of the compositions with or without food.

In certain embodiments the dosage forms comprising the compositions provided herein are in the form of liquid or capsules provided either as blister packages or in bottles together with over the counter medical use information and/or nutritional information.

The packaged pharmaceutical kits can comprise one or more of the compositions described herein as the only active ingredient. In other embodiments, one or more of the compositions described herein can be packaged in combination with one or more active agents other than a non-Omega 3 ester, such as for example and without limitation, one or more other lipid lowering or cholesterol lowering agents selected from the group consisting of cholesterol absorption inhibitors, bile acid sequestrants/resins, statins, niacin and derivatives, MTP inhibitors, fibrates and CETP inhibitors.

Dosage Forms

Any of the compositions provided herein comprising at least one Omega-3 fatty acid ester can be provided as a pharmaceutical composition, a nutraceutical formulation, or a dietary supplement.

The pharmaceutical compositions described herein may further include one or more pharmaceutically acceptable excipients. Pharmaceutically acceptable excipients include, but are not limited to, carriers, preservatives, and/or coloring agents. General considerations in the composition and/or manufacture of pharmaceutical compositions may be found, for example, in Remington The Science and Practice of Pharmacy 21st ed., Lippincott Williams & Wilkins, 2005.

In certain embodiments, the compositions described herein can be formulated as a liquid for oral administration. Liquid compositions include solutions, suspensions and emulsions. Examples of liquid pharmaceutical preparations include propylene glycol solutions and solutions containing sweeteners for oral solutions, suspensions and emulsions. When the liquid composition comes into contact with an aqueous medium, such as for example an aqueous medium having an acidic environment, the composition forms micelles.

In certain embodiments, the dosage form comprises micelles pre-formed prior to administration to a subject in need of such administration. Such pre-formed micelles are stable at room temperature.

In other embodiments, the compositions described herein can be formulated as a fill material for a soft gelatin capsule. Likewise, when the contents of the soft gelatin capsule comes into contact with an aqueous medium, the composition forms micelles upon disintegration of the capsule.

A capsule may be prepared, e.g., by placing the compositions described above inside a capsule shell. A capsule is a dosage form administered in a special container or enclosure containing an active agent. In some embodiments the compositions described herein can be filled into soft capsules. A capsule shell may be made of methylcellulose, hydroxypropylmethyl cellulose, polyvinyl alcohols, or denatured gelatins or starch or other material. Hard shell capsules are typically made of blends of relatively high gel strength bone and pork skin gelatins. In some embodiments the unit dosage form is a gel capsule. In some embodiments the capsule shell is a glycerin capsule shell, for example product no. GSU0051 manufactured by SwissCaps and which meets USP 25 requirements (SwissCaps, USA 14193 SW 119th Ave., Miami/Fla., U.S. 33186). In other embodiments the capsule is a bovine gelatin shell, for example SwissCaps product no. GSU0708. Other suitable capsule shell materials include polyethylene, polypropylene, poly(methylmethacrylate), polyvinylchloride, polystyrene, polyurethanes, polytetrafluoroethylene, nylons, polyformaldehydes, polyesters, cellulose acetate, and nitrocellulose. The capsule shell itself may contain small amounts of dyes, opaquing agents, plasticizers, and preservatives. Conventional methods for preparing other solid dosage forms, for example, capsules, suppositories, and the like are also well known. Gelatin capsule shells may be made also be made of tapioca, grass, vegetable derived or fish derived gelatin. For example K-CAPS (Capsuline, Inc. Pompano Beach, Fla.) is a certified Kosher soft capsule shell of vegetable origin. Other vegetarian derived gelatin capsules may, be made of vegetable derived hydroxypropylmethyl cellulose (HPMC). Capsules shells may also contain Modified Maize Starch, Glycerol, and Carrageenan as a gelling agent.

In other embodiments the capsule has a shell comprising the material of the rate-limiting membrane, including coating materials, and filled with the compositions described herein. Capsule shells may be made of a porous or a pH-sensitive polymer made by a thermal forming process. In certain embodiments the capsule shell in the form of an asymmetric membrane; i.e., a membrane that has a thin skin on one surface and most of whose thickness is constituted of a highly permeable porous material.

Yet another useful capsule, a "swelling plug device", can be used. The compositions described herein can be incorporated into a non-dissolving capsule-half of the device which is sealed at one end by a hydrogel plug. This hydrogel plug swells in an aqueous environment, and, after swelling for a predetermined time, exits the capsule thus opening a port through which the active agent can leave the capsule and be delivered to the aqueous environment. Preferred hydrogel-plugged capsules are those which exhibit substantially no release of active agent from the dosage form until the dosage form has exited the stomach and has resided in the small intestine for about 15 minutes or more, preferably about 30 minutes or more, thus assuring that minimal Omega-3 fatty acid ester is released in the stomach or the small intestine. Hydrogel-plugged capsules of this type have been described in patent application WO90/19168.

The dosage forms may contain a plasticizer, particularly in a capsule shell. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose, triacetin, glycerin, sorbitol, sorbitan or combinations thereof.

In additional embodiments, the compositions can be formulated as a liquid for parenteral administration.

Compositions can be formulated as one or more dosage units. In some embodiments, it can be advantageous to formulate oral compositions in dosage unit form for ease of administration and uniformity of dosage. Dosage unit forms described in some embodiments can refer to physically discrete units suited as unitary dosages for the subject to be treated; each unit containing a predetermined quantity of active composition calculated to produce the desired therapeutic effect in association with the suitable pharmaceutical carrier. In certain embodiments, the dosage form may optionally contain a flavorant such as orange oil, substantially pure d-limonene, and an antioxidant such as tocopherol, ascorbyl palmitate or a combination of antioxidants.

Functional Foods

In certain embodiments, the compositions described herein comprise micelles pre-formed prior to administration to a subject in need of such administration. Such pre-formed micelles are stable at room temperature.

Accordingly, either such pre-formed micelles or the pre-micellized compositions described herein can be added to foods, which can then be consumed as part of a healthy diet for enriching a subject's Omega-3 fatty acid levels or as a dietary treatment in addition to the oral/parenteral administration of the compositions described herein as prescribed by a health professional.

In certain embodiments, the functional food is in the form of edible or drinkable compositions, e.g., foodstuffs such as chewable or edible bars, confectionary products (e.g., chocolate bars), cookies, juice drinks, baked or simulated baked goods (e.g., brownies), biscuits, lozenges or chewing gum. Examples of chewable or edible bars include chocolate bars or energy bars. Such functional foods can be particularly useful to people participating in sports or other forms of exercise.

In certain embodiments, the functional foods may also be in the form of, for example, butter, margarine, bread, cake, milk shakes, ice cream, yogurt and other fermented milk product.

In certain embodiments, the functional food can also be in the form of a liquid to be sprayed on meats, salads or other foods.

Other forms of the functional foods can be breakfast cereals, such as for example, grain flakes, muesli, bran, oatmeal.

When the functional food product is in a drinkable form, the compositions described herein can be added directly to the drink, such as for example plain milk, flavored milk, fermented milk products or juices. The compositions will form micelles comprising the Omega-3 fatty acid esters in the drinkable product.

When the functional food is in the form of a solid edible product, the compositions described herein can be first added to an aqueous medium, wherein the composition will form micelles as described herein. The aqueous medium comprising the micelles can subsequently be either sprayed onto the solid edible product or mixed into the ingredients when manufacturing the edible product.

The invention is further defined by reference to the following examples, which are not meant to limit the scope of the present invention. It will be apparent to those skilled in the art that many modifications, both to the materials and methods, may be practiced without departing from the purpose and interest of the invention.

NON-LIMITING WORKING EXAMPLES

Example 1

The amounts and percentages of the ingredients comprising the composition are shown in Table 1:

TABLE 1

| COMPOSITION (FILL MASS)/dosage form | | |
|---|---|---|
| INGREDIENT | Amount (mg) | % (wt/wt) |
| Total Omega-3 fatty acid Ethyl Esters | 754.3 | 68.57 |
| EPA Ethyl Esters | 392.2 | 35.65 |
| DHA Ethyl Esters | 165.9 | 15.08 |
| Polysorbate 80 | 337.9 | 30.72 |
| PLURONIC ® F87 | 7.8 | 0.71 |

| GEL MASS/dosage form | | |
|---|---|---|
| INGREDIENT | Amount (gm) | % (wt/wt) |
| Gelatin | 270 | 40 |
| Glycerin | 135 | 20 |
| Purified water | 270 | 40 |

The manufacturing process for the dosage form comprising one embodiment of the composition can be separated into three stages: a) the process for manufacturing the composition (fill mass), b) the process for manufacturing the gel mass used for encapsulating the fill mass, and c) the encapsulation process. Stages (a) and (b) can be carried out in either order.

The process for manufacturing the composition begins by weighing appropriate amounts of the Polysorbate 80 and PLURONIC® F87 as per the desired batch size and mixing them to homogeneity at 60° C. in a stainless steel tank. This mixture is allowed to cool to room temperature before the substantially pure Omega-3 fatty acid ethyl ester mixture is vacuum-transferred quantitatively into the same stainless steel tank containing the Polysorbate 80 and PLURONIC® F87. This mixture is again mixed to homogeneity at room temperature before being blanketed with nitrogen. This final composition is also termed the "fill mass".

The process for manufacturing the gel mass begins by weighing appropriate amounts of each of the glycerin and water as per the desired batch size and mixing them to homogeneity in a separate stainless steel mixer at about 80° C. Next, the appropriate amount of gelatin is weighed as per the batch size, added to the glycerin/water mixture and again mixed to homogeneity at 80° C. before being degassed under vacuum. This final mixture comprising glycerin/water/gelatin is termed the "gel mass".

Depending on the desired shape of the capsule, suitable dies and transfer tubing are installed into a soft gel encapsulation apparatus (SS-60 Softgel Encapsulation Machine by SKY Softgel Co. Ltd., Incheon, Korea). The fill mass is pumped into the dies containing a pre-formed ribbon comprising the semi-solid gel mass. The dies shape the soft gelatin capsules, which are then tumble dried for about 20-60 min.

The capsules are transferred onto a tray and dried in a low-temperature/humidity drying room and dried until the capsules reach above 75 shore hardness. The capsules are then inspected, sorted, polished, printed and packaged into bottles. The bottles are affixed with a label, which includes prescribing information. Alternatively, the bottles can be packaged into boxes with a package insert, which includes prescribing information.

Example 2

Experiments were conducted to determine micelle formation in two compositions, A and B, as shown in Table 2. Both compositions were prepared as described in Example 1 comprising Omega-3 fatty acid ethyl esters, in which the Omega-3 fatty acid ethyl esters had increased absorption and the food effect was substantially eliminated.

TABLE 2

| Ingredients | % (wt/wt) | |
| --- | --- | --- |
| | Composition A | Composition B |
| Omega-3 fatty acid Ethyl Esters | 68.57 | 75.0 |
| Polysorbate 80, NF | 30.71 | 20.0 |
| PLURONIC ® F87 | 0.71 | 5.0 |
| Combined surfactant HLB | 15.3 | 16.8 |
| Whole Product HLB | 13 | 13.2 |

The compositions which formed well dispersed micelles generally had a combined surfactant HLB value of about 15 to about 17.

Other compositions with Polysorbate 80 levels between 27-29% in combination with PLURONIC® F87 between about 7% to about 22% generally formed large oil globules. These compositions had a combined surfactant HLB value of from about 17 to about 19. Based on these experiments the whole product HLB was from about 13 and about 14.4 and the combined surfactant HLB was between about 12 to about 17.

Example 3

Compositions A and B (1,000 mg), as shown in Table 2, were added to separate containers containing 500-900 mL of water in 0.1N HCl, under United States Pharmacopeia (USP) dissolution 2 conditions, as described in General Chapter 711, United States Pharmacopeia, 34/National/2011, and observed. Neither composition was subjected to any agitation or shearing. When observed under the microscope, very small, well dispersed micelles were visible. The micelles were stable for over twelve months at room temperature and there was no apparent separation of the Omega-3 fatty acid esters from the other ingredients of the composition. Thus, compositions that included Polysorbate 80 levels between 20-31% in combination with PLURONIC® F87 at 0.7 to 5% formed stable micelles.

Example 4

A human subject ingested composition A in Example 2 (the "Experimental Composition") and underwent blood monitoring to measure the increase in absorption of the Omega-3 fatty acid ethyl esters compared to the Omega-3 fatty acid ethyl esters in an Omega-3 fatty acid ethyl ester composition that is representative of currently marketed drug and nutritional Omega-3 products (the "Standard Composition"). The Standard Composition was manufactured by encapsulating Omega-3 ethyl esters using standard encapsulating methods. Absorption of Omega-3 fatty acid ethyl esters was determined by comparing changes in subject's OmegaIndex following ingestion of the compositions, as measured using the OmegaIndex test kit by OmegaQuant. Prior to ingestion of a composition, blood was drawn from the subject to determine subject's baseline OmegaIndex. The subject then ingested soft gel capsules containing either the Experimental Composition or the Standard Composition. A subsequent blood draw occurred at four hours post-ingestion. The subject remained in the fasted state from the initial baseline blood draw through the four-hour blood draw. The results are shown in Table 4.

TABLE 4

| Capsule Composition | Dose EPA + DHA Ethyl Esters | Omega Index | | |
| --- | --- | --- | --- | --- |
| | | Initial | 4 hour | Increase |
| Standard Composition | 1.52 g | 5.2 | 5.3 | 1.92% |
| Experimental Composition - Dose A (4 capsules, 400 mg total fill weight per capsule) | 1.46 g | 5.4 | 5.7 | 5.55% |
| Experimental Composition - Dose B (10 capsules, 400 mg total fill weight per capsule) | 3.65 g | 4.9 | 5.3 | 8.16% |

Example 5

An Open-label, Randomized, 3 arm, Parallel group, Proof of Concept Study was conducted to evaluate the serum TG lowering efficacy and safety of SC401 Capsules 1100 mg (manufactured as described in Example 1) vs. LOVAZA® (Omega-3-acid ethyl esters) Capsules 1000 mg vs. PLACEBO in hypertriglyceridemic subjects with serum TG between 250 and 500 mg/dL when dosed under fasting conditions.

The aim of this study was to evaluate the effectiveness of SC401 vs. LOVAZA® vs. Placebo on TG reduction over 14 days of treatment. 45 subjects were enrolled in the study in order to complete at least 12 subjects in each of the three treatment arms.

The following inclusion and exclusion criteria were used to select the subjects for this study:

Inclusion Criteria:

Men and women 18 years of age or older;

Serum TG between 200 and 500 mg/dL.

Normally active and in good health on the basis of medical history, brief physical examination, electrocardiogram, and routine laboratory tests.

Be neither over weight nor under weight for his/her height as per the attached height/weight table values (see attached height/weight table).

Provide written informed consent.

If female and of child bearing potential; is practicing an acceptable method of birth control for the duration of the study as judged by the investigator (s), such as condoms, foams, jellies, diaphragm, intrauterine device (IUD), or abstinence; or is postmenopausal for at least 1 year; or is surgically sterile (bilateral tubal ligation, bilateral oophorectomy, or hysterectomy).

Exclusion Criteria:

Severe hypertriglyceridemia (serum TG>500 mg/dL).

Intolerance to Omega-3 or fish.

Use of Omega-3 fish oil, other EPA or DHA and/or DHA fortified foods or other TG lowering medications within three months of study drug initial administration, or during the study.

Consumption of any fish within seven days of study drug initial administration or during the study.

Recent history of certain heart, kidney, liver, lung, or gastrointestinal diseases or cancer (except non-melanoma skin cancer).

Diabetes or receiving insulin therapy.

Pregnant or lactating females. Women of childbearing potential who are not using a medically approved method of contraception.

Use of certain types of hormones, anticonvulsant drugs, immunologic drugs, antibiotic, antifungal and antiviral drugs, and cardiac drugs.

Use of warfarin (Coumadin).

Recent history (past 12 month) of drug abuse or alcohol abuse.

Exposure to any investigational product, within 28 days prior to study drug administration.

Subjects diagnosed with the following conditions:

Endocrine diabetes mellitus, hypothyroidism, pregnancy;

Nutritional obesity, alcohol access;

Renal nephrotic disease, chronic renal failure;

Hepatic disease cholestas, hepatocellular dysfunction;

Immunoglobulin excess paraproteinemia;

Gout;

Any other condition the investigator believes would interfere with the patient's ability to provide informed consent, comply with study instructions, or which might confound the interpretation of the study results or put the patient at undue risk; and subjects on the following medications Thiazide diuretic, Steroid hormones, Microsomal enzyme, Retinoic acid derivatives, Protease inhibitors (HIV infection).

The Informed Consent Document (ICD) was read by the volunteer and signed prior to study specific procedures. Additionally, the following tests were be performed at clinic entry for each period Urine screen for drugs of abuse—including cocaine, *cannabis*, amphetamines, barbiturates, benzodiazepines and opiates. Subjects were rejected/withdrawn from the study if the result was positive for these drugs, Alcohol breath test—subjects were rejected/withdrawn from the study if the result was positive for alcohol, Urine pregnancy test (HCG) (for female subjects only)—Female subjects were rejected/withdrawn from the study if result was positive for pregnancy, and Gynecological & breast examination (for female subjects only)—subjects were rejected/withdrawn from the study if there were any abnormalities in the examination.

Subjects were housed in the clinical facility from at least 48 hours pre-dose to at least 14 days and were requested to stay for 16 consecutive nights in the facility.

Subjects were fasted for at least 10 hours before morning dosing and were instructed to abstain from consuming caffeine and/or xanthine containing products (i.e. coffee, tea, chocolate, and caffeine-containing sodas, colas, etc.), alcohol and vitamin supplements, including vitamin C and ascorbic acid and grapefruit and its juice, for at least 48 hours prior to dosing and throughout the study. No citrus juices, including orange juice and grapefruit juice, were provided during the study.

After overnight fast of 10 hours subjects were dosed under monochromatic light or low light condition as follows:

SC401 (Omega-3 Fatty Acid Ethyl Esters, 1100 mg) 2 capsules (as single dose), taken upon awakening (at least 2 hours before breakfast taken with water only on an empty stomach); then 2 capsules (as single dose) taken at bedtime (at least 2 hours after dinner taken with water only and no food or liquids thereafter for the night), or LOVAZA® (Omega-3 Fatty Acid Ethyl Esters, 1000 mg, of GlaxoSmithKline, RTP, NC 2770) 2 capsules (as single dose) taken upon awakening (at least 2 hour before breakfast taken with water only on an empty stomach); then 2 capsules (as single dose) taken at bedtime (at least 2 hours after dinner taken with water only and no food or liquids thereafter for the night), or PLACEBO (Ethyl Oleate, 1000 mg capsules) 2 capsules (as single dose) taken upon awakening (at least 2 hour before breakfast taken with water only on an empty stomach); then 2 capsules (as single dose) taken at bedtime (at least 2 hours after dinner taken with water only and no food or liquids thereafter for the night).

The amounts of Omega-3 fatty acid ethyl esters comprising LOVAZA®, SC401 and the placebo are shown in the Table 5 below:

TABLE 5

| Capsule Fill Composition (mg) | SC401 | LOVAZA ® | Placebo |
|---|---|---|---|
| Total Omega-3 Fatty Acid Ethyl Esters | 754.3 | 934 | 0 |
| EPA Ethyl Esters | 392.2 | 482 | 0 |
| DHA Ethyl Esters | 165.9 | 370 | 0 |
| Polysorbate 80, NF | 337.9 | 0 | 0 |
| PLURONIC ® F87 | 7.8 | 0 | 0 |
| Ethyl Oleate | 0 | 0 | 1000 |

4 blood samples (8 mL each) were collected over the study period. The blood samples will be collected at $T_s$, $T_0$, $T_{7d}$, $T_{14d}$ in plain vacuum tubes by direct vein puncture. Vacutainers were placed upright in a rack kept in wet ice bath until transferred to Diagnostic department.

For $T_s$, $T_0$, $T_{7d}$, $T_{14d}$, fasting triglyceride/HDL/LDL/total cholesterol/non-HDL/levels for each patient in each of three groups was determined.

The data are tabulated in Table 6 below:

TABLE 6

| | Results at Day 14 from Baseline* | | |
|---|---|---|---|
| | SC401 | LOVAZA ® | Placebo |
| Serum blood levels of triglycerides | −48.5% | −29.4% | −27.7% |

*SC401 results adjusted to match amount of total EPA and DHA ethyl esters dosed in LOVAZA ® arm.

That which is claimed:

1. A pharmaceutical composition which self-micellizes upon contact with an aqueous medium to form spherical micelles which have an average diameter of from about 1 μm to about 10 μm, or stable micelles pre-formed from said composition, and which provide for absorption of omega-3 fatty acid esters substantially free of any food effect, said pharmaceutical composition comprising:
a) from about 60% (wt/wt)-about 85% (wt/wt) of a mixed-fatty-acids composition, wherein from about 80% to about 90% of said mixed-fatty-acids composition is a combination of (all-Z omega-3)-5,8,11,14,17-eicosapentaenoic acids (EPA) and (all-Z omega-3)-4,7,10,13,16,19-docosahexaenoic acids (DHA) in a weight ratio of EPA:DHA of from about 1:2 to about 2:1;
b) (all-Z omega-3)-6,9,12,15,18-heneicosapentaenoic acid in an amount of at least one percent by weight of the composition; and
c) a surface active agent which comprises, in combination, at least one non-ionic polyoxyethylene glycol sorbitan alkyl ester (a polysorbate) selected from the group consisting of polyoxyethylene (20) sorbitan monolaurate (polysorbate 20), polyoxyethylene (20) sorbitan monopalmitate (polysorbate 40), (polyoxyethylene (20) sorbitan monostearate (polysorbate 60) and polyoxyethylene (20) sorbitan monooleate (polysorbate 80); and a block copolymer of polyethylene glycol and polypropylene glycol having the formula [(HO(C2H4O)64(C3H6O)37 (C2H4O)64H] (Poloxamer 237);
wherein said polysorbate is present in an amount within the range of about 15% (wt/wt) to about 31% (wt/wt) of said pharmaceutical composition; and said Poloxamer 237 is present in an amount within the range of about 5% (wt/wt) to about 5% (wt/wt) of said pharmaceutical composition;
whereby said combination of surface active agents are effective to form said stable micelles upon contact with said aqueous medium;
wherein said composition is free of active ingredients other than omega-3 fatty acid esters; and wherein said composition when administered to a human at equal dosage strengths provides for substantially the same bioavailability when administered with or without food to said human in need of such administration; and
whereby said pharmaceutical composition self-micellizes in an aqueous medium, thus forming spherical micelles having an average diameter of from about 1 μm to about 10 μm, which provide for absorption of said omega-3 fatty acid esters substantially free of any food effect.

2. The composition of claim 1 wherein said mixed fatty acids are ethyl esters.

3. The composition of claim 1 further comprising from about 0.1% to about 5% (wt/wt) of the composition of natural orange oil, or from about 0.1% to about 5% (wt/wt) of the composition of substantially pure d-limonene, or a combination thereof.

4. The composition of claim 1 further comprising an effective amount of a pharmaceutically acceptable antioxidant.

5. A method for the treatment of multiple risk factors for cardiovascular diseases in a subject in need thereof which comprises administering orally or parenterally to said subject the composition of claim 1, or stable micelles pre-formed therefrom, in a daily therapeutically effective amount of about 0.5 g to about 10 g, for a period of time effective to reduce one or more of said multiple risk factors.

6. The method of claim 5 wherein said composition or said pre-formed stable micelles are in a liquid or capsule dosage form.

7. A pharmaceutical composition for the treatment of multiple risk factors for cardiovascular diseases, which self-micellizes upon contact with an aqueous medium to form spherical micelles which have an average diameter of from about 1 μm to about 10 μm, or stable micelles pre-formed from said composition, and which provide for absorption of omega-3 fatty acid esters substantially free of any food effect, said pharmaceutical composition comprising:
a) from about 60% (wt/wt)-about 85% (wt/wt) of a mixed-fatty-acids composition, wherein from about 80% to about 90% of said mixed-fatty-acids composition is a combination of (all-Z omega-3)-5,8,11,14,17-eicosapentaenoic acids (EPA) and (all-Z omega-3)-4,7,10,13,16,19-docosahexaenoic acids (DHA) in a weight ratio of EPA:DHA of from about 1:2 to about 2:1;
b) Omega-3 fatty acids other than EPA and DHA are present in an amount of about 1.5% by weight of said mixed fatty acids composition; and
c) a surface active agent which comprises, in combination, at least one non-ionic polyoxyethylene glycol sorbitan alkyl ester (a polysorbate) selected from the group consisting of polyoxyethylene (20) sorbitan monolaurate (polysorbate 20), polyoxyethylene (20) sorbitan monopalmitate (polysorbate 40), (polyoxyethylene (20) sorbitan monostearate (polysorbate 60) and polyoxyethylene (20) sorbitan monooleate (polysorbate 80); and a block copolymer of polyethylene glycol and polypropylene glycol having the formula [(HO(C2H4O)64(C3H6O)37(C2H4O)64H] (Poloxamer 237);
wherein said polysorbate is present in an amount within the range of about 15% (wt/wt) to about 31% (wt/wt) of said composition; and said Poloxamer 237 is present in an amount within the range of about 0.5% (wt/wt) to about 5% (wt/wt) of said composition;
whereby said combination of surface active agents are effective to form said stable micelles upon contact with said aqueous medium;
wherein said composition is free of active ingredients other than omega-3 fatty acid esters; and wherein said composition when administered to a human at equal dosage strengths provides for substantially the same bioavailability when administered with or without food to said human in need of such administration; and
whereby said pharmaceutical composition self-micellizes in an aqueous medium, thus forming spherical micelles having an average diameter of from about 1 μm to about 10 μm, which provide for absorption of said omega-3 fatty acid esters substantially free of any food effect.

8. The composition of claim 7 wherein said mixed fatty acids are ethyl esters.

9. The composition of claim 7 further comprising from about 0.1% to about 5% (wt/wt) of the composition of natural orange oil, or from about 0.1% to about 5% (wt/wt) of the composition of substantially pure d-limonene, or a combination thereof.

10. The composition of claim 7 further comprising an effective amount of a pharmaceutically acceptable antioxidant.

11. A method for the treatment of multiple risk factors for cardiovascular diseases in a subject in need thereof which comprises administering orally or parenterally to said subject the composition of claim 7, or stable micelles pre-formed therefrom, in a daily therapeutically effective amount of about 0.5 g to about 10 g, for a period of time effective to reduce one or more of said multiple risk factors.

12. The method of claim 11 wherein said composition or said pre-formed stable micelles are in a liquid or capsule dosage form.

13. A pharmaceutical composition for the treatment of multiple risk factors for cardiovascular diseases, which self-micellizes upon contact with an aqueous medium to form spherical micelles which have an average diameter of from about 1 µm to about 10 µm, or stable micelles pre-formed from said composition, and which provide for absorption of omega-3 fatty acid esters substantially free of any food effect, said pharmaceutical composition comprising:
  a) from about 60% (wt/wt)-about 85% (wt/wt) of a mixed-fatty-acids composition, wherein from about 80% to about 90% of said mixed-fatty-acids composition is a combination of (all-Z omega-3)-5,8,11,14,17-eicosapentaenoic acid (EPA) and (all-Z omega-3)-4,7,10,13,16, 19-docosahexaenoic acid (DHA) in a weight ratio of EPA:DHA of from 1:2 to 2:1,
  b) at least 3% by weight of said mixed fatty acids composition is comprised of Omega-3 fatty acids other than EPA and DHA that have 18, 20, 21, or 22 carbon atoms, and
  c) a surface active agent which comprises, in combination, at least one non-ionic polyoxyethylene glycol sorbitan alkyl ester (a polysorbate) selected from the group consisting of polyoxyethylene (20) sorbitan monolaurate (polysorbate 20), polyoxyethylene (20) sorbitan monopalmitate (polysorbate 40), (polyoxyethylene (20) sorbitan monostearate (polysorbate 60) and polyoxyethylene (20) sorbitan monooleate (polysorbate 80); and a block copolymer of polyethylene glycol and polypropylene glycol having the formula [(HO(C2H4O)64 (C3H6O)37(C2H4O)64H] (Poloxamer 237);
  wherein said polysorbate is present in an amount within the range of about 15% (wt/wt) to about 31% (wt/wt) of said pharmaceutical composition; and said Poloxamer 237 is present in an amount within the range of about 0.5% (wt/wt) to about 5% (wt/wt) of said pharmaceutical composition;
  whereby said combination of surface active agents are effective to form said stable micelles upon contact with said aqueous medium;
  wherein said composition is free of active ingredients other than omega-3 fatty acid esters; and wherein said composition when administered to a human at equal dosage strengths provides for substantially the same bioavailability when administered with or without food to said human in need of such administration; and
  whereby said pharmaceutical composition self-micellizes in an aqueous medium, thus forming spherical micelles having an average diameter of from about 1 µm to about 10 µm, which provide for absorption of said omega-3 fatty acid esters substantially free of any food effect.

14. The composition of claim 13 wherein said mixed fatty acids are ethyl esters.

15. The composition of claim 13 further comprising from about 0.1% to about 5% (wt/wt) of the composition of natural orange oil, or from about 0.1% to about 5% (wt/wt) of the composition of substantially pure d-limonene, or a combination thereof.

16. The composition of claim 13 further comprising an effective amount of a pharmaceutically acceptable antioxidant.

17. A method for the treatment of multiple risk factors for cardiovascular diseases in a subject in need thereof which comprises administering orally or parenterally to said subject the composition of claim 13, or stable micelles pre-formed therefrom, in a daily therapeutically effective amount of about 0.5 g to about 10 g, for a period of time effective to reduce one or more of said multiple risk factors.

18. The method of claim 17 wherein said composition or said pre-formed stable micelles are in a liquid or capsule dosage form.

19. A pharmaceutical composition for the treatment of multiple risk factors for cardiovascular diseases, which self-micellizes upon contact with an aqueous medium to form spherical micelles which have an average diameter of from about 1 µm to about 10 µm, or stable micelles pre-formed from said composition, and which provide for absorption of omega-3 fatty acid esters substantially free of any food effect, said pharmaceutical composition comprising:
  a) from about 60% (wt/wt)-about 85% (wt/wt) of a mixed-fatty-acids composition, wherein about 90% by weight of the mixed-fatty-acids composition is comprised of long chain, polyunsaturated, Omega-3 fatty acids;
  b) wherein from about 80% to about 90% of said long chain, polyunsaturated, Omega-3 fatty acids in said mixed-fatty-acids composition is a combination of (all-Z omega-3)-5,8,11,14,17-eicosapentaenoic acid (EPA) and (all-Z omega-3)-4,7,10,13,16,19-docosahexaenoic acid (DHA) in a weight ratio of EPA:DHA of from 1:1 to 2:1, with the EPA constituting 40 to 60% by weight of the mixed-fatty-acids composition and the DHA constituting 25 to 45% by weight of the mixed-fatty-acids composition;
  c) at least 4.5% by weight of the mixed fatty acids composition is comprised of Omega-3 fatty acids other than EPA and DHA that have 18, 20, 21, or 22 carbon atoms;
  d) from 1 to 4% by weight of the mixed fatty acids composition is comprised of (all-Z omega-3)-6,9,12,15,18-heneicosapentaenoic acid; and
  e) a surface active agent which comprises, in combination, at least one non-ionic polyoxyethylene glycol sorbitan alkyl ester (a polysorbate) selected from the group consisting of polyoxyethylene (20) sorbitan monolaurate (polysorbate 20), polyoxyethylene (20) sorbitan monopalmitate (polysorbate 40), (polyoxyethylene (20) sorbitan monostearate (polysorbate 60) and polyoxyethylene (20) sorbitan monooleate (polysorbate 80); and a block copolymer of polyethylene glycol and polypropylene glycol having the formula [(HO(C2H4O)64 (C3H6O)37 (C2H4O)64H] (Poloxamer 237);
  wherein said polysorbate is present in an amount within the range of about 15% (wt/wt) to about 31% (wt/wt) of said composition; and said Poloxamer 237 is present in an amount within the range of about 0.5% (wt/wt) to about 5% (wt/wt) of said composition;
  whereby said combination of surface active agents are effective to form said stable micelles upon contact with said aqueous medium;
  wherein said composition is free of active ingredients other than omega-3 fatty acid esters; and wherein said composition when administered to a human at equal dosage strengths provides for substantially the same bioavailability when administered with or without food to said human in need of such administration; and
  whereby said pharmaceutical composition self-micellizes in an aqueous medium, thus forming spherical micelles having an average diameter of from about 1 µm to about 10 µm, which provide for absorption of said omega-3 fatty acid esters substantially free of any food effect.

20. The composition of claim 19 wherein said mixed fatty acids are ethyl esters.

21. The composition of claim 19 further comprising about 0.1% to about 5% (wt/wt) of the composition of natural orange oil, or from about 0.1% to about 5% (wt/wt) of the composition of substantially pure d-limonene, or a combination thereof.

22. The composition of claim 19 further comprising an effective amount of a pharmaceutically acceptable antioxidant.

23. A method for the treatment of multiple risk factors for cardiovascular diseases in a subject in need thereof which comprises administering orally or parenterally to said subject the composition of claim 19, or stable micelles pre-formed therefrom, in a daily therapeutically effective amount of about 0.5 g to about 10 g, for a period of time effective to reduce one or more of said multiple risk factors.

24. The method of claim 23 wherein said composition or said pre-formed stable micelles are in a liquid or capsule dosage form.

* * * * *